US007265088B1

(12) United States Patent
Li et al.

(10) Patent No.: US 7,265,088 B1
(45) Date of Patent: Sep. 4, 2007

(54) METHOD AND COMPOSITIONS FOR ALTERING MUCUS SECRETION

(75) Inventors: Yuehua Li, Raleigh, NC (US); Linda D. Martin, Apex, NC (US); Kenneth B. Adler, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/914,020

(22) PCT Filed: Feb. 24, 2000

(86) PCT No.: PCT/US00/05050

§ 371 (c)(1),
(2), (4) Date: Dec. 31, 2001

(87) PCT Pub. No.: WO00/50062

PCT Pub. Date: Aug. 31, 2000

(51) Int. Cl.
*A61K 38/16* (2006.01)
*A61K 38/10* (2006.01)

(52) U.S. Cl. .......................... 514/12; 514/13; 514/14; 514/15

(58) Field of Classification Search ................ None
See application file for complete search history.

(56) References Cited

U.S. PATENT DOCUMENTS

| | | | |
|---|---|---|---|
| 4,753,945 A | 6/1988 | Gilbard et al. | 514/263 |
| 4,873,346 A | 10/1989 | Anderson | 548/157 |
| 5,298,506 A | 3/1994 | Stamler et al. | 514/226.2 |
| 5,436,243 A | 7/1995 | Sachs et al. | 514/231.8 |
| 5,849,706 A | 12/1998 | Molina y Vedia et al. | 514/12 |
| 5,849,719 A | 12/1998 | Carson et al. | 514/44 |
| 5,858,784 A | 1/1999 | Debs et al. | 435/375 |
| 5,858,981 A | 1/1999 | Schreiber et al. | 514/18 |
| 5,861,502 A | 1/1999 | Prockop et al. | 536/24.5 |

FOREIGN PATENT DOCUMENTS

| | | |
|---|---|---|
| EP | 0551200 A1 | 7/1993 |
| WO | WO93/00353 | 1/1993 |
| WO | WO95/27496 | 10/1995 |
| WO | WO96/18103 | 6/1996 |

OTHER PUBLICATIONS

Rogers, Duncan. Mucus hypersecretion in chronic obstructive pulmonary disease. Chronic Obstructive Pulmonary Disease: Pathogenesis to Treatment: Novartis Foundation. Symposium 234. vol. 234. Copyright © Novartis Foundation. 2001. ISBN:0-471-49437-2.*
Barnes, Peter J. Current and Future therapeies for airway mucus hypersecretion. Novartis Foundation Symposium, vol. 248. Copyright © Novartis Foundation, 2002. ISBN: 0-470-84478-7, pp. 237-253.*
Rogers, Duncan F. (2003) Pulmonary Mucus: Pediatric Perspective. Pediatric Pulmonology, vol. 36: 178-188.*
Ward et al. 1994, Therapeutic Immunology. vol. 1, pp. 165-171.*
Singer et al., *A MARCKS-related peptide blocks mucus hypersecretion in a mouse model of asthma*, Nature Medicine, vol. 10, No. 2, Feb. 2004, pp. 193-196.
International Search Report, PCT/US00/05050, Sep. 29, 2000.
Adler et al., *Myristoylated Alanine-Rich C-Kinase Substrate Protein: A Major Intracellular Regulatory Molecule Controlling Secretion of Mucin by Human Airway Goblet Cells*, Chest, vol. 117, 2000, pp. 266S-267S.
Adler et al., *Effects of Inflammatory Mediators and Drugs on Mucus Secretion and Mucociliary Function*, Research in Immunology, vol. 149, 1998 pp. 245-248.
Lu et al., *Regulation of Angiotensin II-Induced Neuromodulation by MARCKS in Brain Neurons*, The Journal of Cell Biology, vol. 142, No. 1, Jul. 13, 1998, pp. 217-227.
Nakamura et al., *Mucin-Like Glycoprotein Secretion is Mediated by Cyclic-AMP and Protein Kinase C Signal Transduction Pathways in Rat Corneal Epithelium*, Experimental Eye Research, vol. 66, 1998, pp. 513-519.
Myat et al., *Identification of the Basolateral Targeting Determinant of a Peripheral Membrane Protein, MacMARCKS, in Polarized Cells*, Current Biology, vol. 8, 1998, pp. 677-683.
Gipson et al., Abstract of *Cellular Origin of Mucins of the Ocular Surface Tear Film*, Adv. Exp. Med. Biol., vol. 438, 1998, pp. 221-227.
Garcher et al., Abstract of *CA 19-9 ELISA Test: A New Method for Studying Mucus Changes in Tears*, Br. J. Ophthalmol., vol. 82, No. 1, Jan. 1998, pp. 88-90.
Dray-Charier et al., *Regulation of Mucin Secretion in Human Gallbladder Epithelial Cells: Predominant Role of Calcium and Protein Kinase C*, Gastroenterology, vol. 112, 1997, pp. 978-990.
Raufman et al, *Expression and Phosphorylation of a MARCKS-Like Protein in Gastric Chief Cells: Further Evidence for Modulation of Pepsinogen Secretion by Interaction of $Ca^{2+}$ /Calmodulin With Protein Kinase C*, Journal of Cellular Biochemistry, vol. 64, 1997, pp. 514-523.
Ko et al., *ATP-Induced Mucin Release From Cultured Airway Goblet Cells Involves, in Part, Actvation of Protein Kinase C*, Am. J. Respir. Cell Mol. Biol., vol. 16, 1997, pp. 194-198.
Abdullah et al., *Protein Kinase C and $Ca^{2+}$ Activation of Mucin Secretion in Airway Goblet Cells*, American Journal of Physiology, 273 (Lung Cellular and Molecular Physiology 17), 1997, pp. L201-L210.

(Continued)

*Primary Examiner*—Janet Epps-Ford
(74) *Attorney, Agent, or Firm*—Myers Bigel Sibley & Sajovec, P.A.

(57) ABSTRACT

Methods and compounds for increasing or decreasing mucus secretion in subjects, and particularly mucus secretion in the airways, are described. Methods of screening compounds for the ability to increase or decrease mucus secretion are also described.

10 Claims, 9 Drawing Sheets

OTHER PUBLICATIONS

Mastropasqua et al., Abstract of *Tear Deficiency in Fuchs' Intermediate Uveitis*, Can. J. Ophthalmol., vol. 31, No. 1, Feb. 1996, pp. 18-20.

Adler et al., *Hypersection of Mucin in Response to Inflammatory Mediators by Guinea Pig Tracheal Epithelial Cells In Vitro Is Blocked by Inhibition of Nitric Oxide Synthase*, Am. J. Respir. Cell Mol. Biol., vol. 13, 1995, pp. 526-530.

Aderem, *The MARCKS Family of Protein Kinase-C Substrates*, Biochemical Society Transactions, vol. 23, 1995, pp. 587-591.

Stormshak et al., *Dynamics of Molecular Mechanisms Underlying Ovarian Oxytocin Secretion*, Journal of Reproduction and Fertility Supplement, vol. 49, 1995, pp. 379-390.

Kessler et al., Abstract of *Stimulation of Goblet Cell Mucous Secretion by Activation of Nerves in Rat Conjunctiva*, Curr. Eye Res., vol. 14, No. 11, Nov. 1995, pp. 985-992.

Vergéres et al., *The Myristoyl Moiety of Myristoylated Alanine-Rich C Kinase Susbtrate (MARCKS) and MARCKS-Related Protein Is Embedded in the Membrane*, The Journal of Biological Chemistry, vol. 270, No. 34, Aug. 25, 1995, pp. 19879-19887.

Lui et al., *Arginine Vasopressin (AVP) Causes the Reversible Phosphorylation of the Myristoylated Alanine-Rich C Kinase Substrate (MARCKS) Protein in the Ovine Anterior Pituitary: Evidence That MARCKS Phosphorylation is Associated With Adrenocorticotropin (ACTH) Secretion*, Molecular and Cellular Endocrinology, vol. 105, 1994, pp. 217-226.

Coffey et al., *Glutamate Exocytosis and MARCKS Phosphorylation are Enhanced by a Metabotropic Glutamate Receptor Coupled to a Protein Kinase C. Synergistically Activated by Diacylglycerol and Arachidonic Acid*, Journal of Neurochemistry, vol. 63, No. 4, 1994, pp. 1303-1310.

Liu et al., *Arginine Vasopressin (AVP) Causes the Reversible Phosphorylation of the Myristoylated Alanine-Rich C Kinase Substrate (MARCKS) Protein in the Ovine Anterior Pituitary: Evidence That MARCKS Phosphorylation is Associated With Adrenocorticotropin (ACTH) Secretion*, Molecular and Cellular Endocrinology, vol. 101, 1994, pp. 247-256.

Aigner et al., *Depletion of 43-kD Growth-Associated Protein in Primary Sensory Neurons Leads to Diminished Formation and Spreading of Growth Cones*, The Journal of Cell Biology, vol. 123, No. 2, Oct. 1993, pp. 417-429.

Calle et al., *Glucose-Induced Phosphorylation of Myristoylated Alanine-Rich C Kinase Substrate (MARCKS) in Isolated Rat Pancreatic Islets*, The Journal of Biological Chemistry, vol. 267, No. 26, Sep. 15, 1992, pp. 18723-18727.

Driot et al., Abstract of *Beneficial Effects of a Retinoic Acid Analog, CBS-211 A, On An Experimetal Model of Keratoconjunctivitis Sicca.*, Invest. Ophthalmol. Vis. Sci., vol. 33, No. 1, Jan. 1992, pp. 190-195.

Graff et al., *Protein Kinase C Susbtrate and Inhibitor Characteristics of Peptides Derived From the Myristoylated Alanine-Rich C Kinase Substrate (MARCKS) Protein Phosphorylation Site Domain*, The Journal of Biological Chemistry, vol. 266, No. 22, Aug. 5, 1991, pp. 14390-14398.

Harlan et al., *The Human Myristoylated Alanine-Rich C Kinase Substrate (MARCKS) Gene (MACS)*, The Journal of Biological Chemistry, vol. 266, No. 22, Aug. 5, 1991, pp. 14399-14405.

Thelen et al., *Regulation by Phosphorylation of Reversible Association of a Myristoylated Protein Kinase C Susbtrate with the Plasma Membrane*, Nature, vol. 351, May 23, 1991, pp. 320-322.

Thelen et al., *Tumor Necrosis Factor α Modifies Agonist-Dependent Responses in Human Neutrophils by Inducing the Synthesis and Myristoylation of a Specific Protein Kinase C Substrate*, Proc. Natl. Acad. Sci., USA, vol. 87, Aug. 1990, pp. 5603-5607.

Linsen et al., Abstract of *Physiology of the Lacrimal System*, Bull Soc. Belge Ophtalmol., vol. 238, 1990, pp. 35-44.

Shellans et al., Abstract of *Conjunctival Goblet Cell Response to Vasoconstrictor Use*, J. Ocul. Pharmacol., vol. 5, No. 3, Fall 1989, pp. 217-220.

Stumpo et al., *Molecular Cloning, Characterization, and Expression of a cDNA Encoding the "80-to 87-kDa" Myristoylated Alanine-Rich C Kinase Substrate; A Major Cellular Substrate of Protein Kinase C*, Proc. Natl. Acad. Sci., USA, vol. 86, 1989, pp. 4012-4016.

Aragona et al., Abstract of *Effects of a Stable Analogue of PGE2 (11-deoxy-13, 14-didehydro-16 (S)-Methylester Methyl PGE2: FCE 20700) on the Secretory Processes on Conjunctival Goblet Cells of Rabbit.*, Exp. Eye Res., vol. 45, No. 5, Nov. 1987, pp. 647-654.

Tseng, Abstract of *Topical Tretinoin Treatment for Severe Dry-Eye Disorders*, J. Am. Acad. Dermatol., vol. 15, No. 4 (Pt. 2), Oct. 1986, pp. 860-866.

Nichols et al., Abstract of *Demonstration of the Mucous Layer of the Tear Film by Electron Microscopy*, Invest. Ophthalmol. Vis. Sci., vol. 26, No. 4, Apr. 1985, pp. 464-473.

Ralph, Abstract of *Conjunctival Goblet Cell Density in Normal Subjects and in Dry Eye Syndromes*, Invest. Ophthalmol., vol. 14, No. 4, Apr. 1975, pp. 299-302.

Abdullah et al. "Protein Kinase C and Ca2+ Activation of Mucin Secretion in Airway Goblet Cells" The American Journal of Physiology 273(1): L201-L210 (1997).

Blackshear "The MARCKS Family of Cellular Protein Kinase C Substrates" Journal of Biological Chemistry 268(3): 1501-1504 (1993).

Graff et al. "Protein Kinase C Substrate an inhibitor Characteristics of Peptides Derived From the Myristoylated Alanine-Rich C Kinase Substrate (MARCKS) Protein Phosphorylation Site Domain" Journal of Biological Chemistry 266:(22): 14390-14398 (1991).

Harlan et al. "The Human Myristoylated Alanine-Rich C Kinase Substrate MARCKS Gene Macs Analysis of its Gene Product Promoter and Chromosomal Localization" Journal of Biological Chemistry 266(22): 14399-14405 (1991).

Kim et al. "Airway Goblet Cell Mucin: its Structure and Regulation of Secretion" The European Respiratory Journal 10(11): 2644-2649 (1997).

Partial European Search Report for European Application No. 04 02 4019 completed on Apr. 19, 2005.

\* cited by examiner

Column 1: Media
Column 2: 0.1 mM UTP
Column 3: 0.1 mM UTP & 1 uM peptide MANS
Column 4: 0.1 mM UTP & 10 uM peptide MANS
Column 5: 0.1 mM UTP & 100 uM peptide MANS Column 1: Media / Control
Column 2: 100 nM PMA & 1 uM 8-Br-cGMP
Column 3: 5 uM Control Oligo / 100 nM PMA & 1 uM 8-Br-cGMP
Column 4: 5 uM Antisense Oligo / 100 nM PMA & 1 uM 8-Br-cGMP

METHOD AND COMPOSITIONS FOR ALTERING MUCUS SECRETION

This application claims priority under 35 U.S.C. § 371 from PCT Application No. PCT/US00/05050 (published under PCT Article 21(2) in English, filed on Feb. 24, 2000, which claims the benefit of U.S. application Ser. No. 09/256,154, filed Feb. 24, 1999, abandoned, the disclosures if which are incorporated by reference herein in their entireties.

FIELD OF THE INVENTION

The present invention relates to methods and compositions that are useful in regulating mucus secretion, and that may be utilized in treating medical conditions where it is desirable to increase or decrease mucus secretion.

BACKGROUND OF THE INVENTION

Mucus is a biological liquid that is capable of forming gels. It is a mixture of components, including water and secretory products from a variety of cells. Expectorated human airway mucus contains approximately 95% water and 5% solids; the solids contents include 2-3% proteins and glycoproteins, 1% lipids, and 1% minerals. See Boat et al., *Biochemistry of Mucus*, In: *Airway Secretion*, Takashima and Shimura (eds.), Marcel Dekker, 1994. Mucins, also called mucous glycoproteins or epithelial glycoproteins, are glycoconjugates characterized by numerous oligosaccharide side chains linked to a peptide core by N- and O-linkages.

In the airways, mucins are released onto the airway surface from goblet cells on the surface epithelium, and from mucus cells of submucosal glands. The total amount of surface liquid (mucus) in the airways is the result of the rate of mucus secretion in conjunction with the rate of clearance of mucus (by epithelial reabsorption, evaporation, ciliary transport, and cough transport). Under "normal" conditions, the rate of secretion and clearance of mucus are balanced so that only a thin surface layer of liquid covers the tracheobronchial tree. Mucus hypersecretion (if not accompanied by a concomitant increase in mucus clearance) results in accumulation of airway mucus, which can result in airflow obstruction and increased retention of inhaled particulate matter and microbial matter. Existing strategies to reduce luminal mucus in the airways include inhibition of mucus hypersecretion using indirect pharmacological action, changing the physical characteristics of mucus to enhance ciliary action, and enhancement of cough clearance of mucus.

Hypersecretion of mucus contributes to the pathogenesis of a large number of airway inflammatory diseases in both human and non-human animals. Increased mucus secretion is seen in chronic disease states such as asthma, COPD and chronic bronchitis; in genetic diseases such as cystic fibrosis; in allergic conditions (atopy, allergic inflammation); in bronchiectasis; and in a number of acute, infectious respiratory illnesses such as pneumonia, rhinitis, influenza or the common cold. Accordingly, new methods and therapeutic compounds able to decrease or lessen mucus secretion are desirable.

Under-secretion of mucus also has harmful effects. Airway mucus acts as a physical barrier against biologically active inhaled particles, and may help prevent bacterial colonization of the airways and inactivate cytotoxic products released from leukocytes. King et al., *Respir. Physiol.* 62:47-59 (1985); Vishwanath and Ramphal, *Infect. Immun.* 45:197 (1984); Cross et al., *Lancet* 1:1328 (1984). In the eye, mucus maintains the tear film, and is important for eye health and comfort. Mucus secretion in the gastrointestinal tract also has a cytoprotective function. The role of mucus as a chemical, biological and mechanical barrier means that abnormally low mucus secretion by mucous membranes is undesirable.

In view of the foregoing, improved methods and compositions able to alter (i.e., increase or decrease) mucus secretion from epithelial cells and mucus membranes are desirable.

SUMMARY OF THE INVENTION

A first aspect of the present invention is a method of inhibiting mucus secretion by a mucus-secreting cell, by administering to the cell a mucus-inhibitory amount of a compound that inhibits MARCKS protein-related mucus secretion.

A second aspect of the present invention is a method of inhibiting mucus secretion by a mucus-secreting cell, by administering to the cell a peptide inhibitor of MARCKS-related mucus secretion.

A third aspect of the present invention is a method of inhibiting mucus secretion in the airways of a subject in need of such treatment, by administering to the airways of the subject a mucus-inhibiting amount of a compound that inhibits the MARCKS-related release of mucin.

A fourth aspect of the present invention is a method of increasing mucus secretion by a mucus-secreting cell, by administering to the cell a secretion-enhancing fragment of a MARCKS protein in an amount sufficient to increase mucus secretion by the cell, compared to that which would occur in the absence of the protein fragment.

A fifth aspect of the present invention is a method of inhibiting mucus secretion by a mucus-secreting cell, by administering to the cell a mucus-inhibiting amount of an antisense construct that specifically binds to endogenous MARCKS protein encoding sequences under physiological conditions, wherein mucus secretion by the cell is inhibited compared to that which would occur in the absence of such administration.

A sixth aspect of the present invention is a pharmaceutical formulation containing a mucus-inhibiting peptide fragment of MARCKS and a pharmaceutically acceptable carrier.

A seventh aspect of the present invention is an oligonucleotide consisting of about 10 to 50 nucleotides having a nucleotide sequence that hybridizes to nucleotide molecules encoding a MARCKS protein under physiologic conditions. The oligonucleotide inhibits expression of the MARCKS protein when administered to a cell containing the endogenous nucleotide molecules.

An eighth aspect of the present invention is a method of inhibiting mucus secretion by a mucus-secreting cell, by administering to the cell a mucus-inhibitory amount of a compound that binds to a target site selected from (a) mucin granule membranes at the site bound by MARCKS protein; and (b) MARCKS protein at the mucin granule binding site. The amount of mucus secreted by the cell is reduced compared to that which would occur in the absence of the compound.

A ninth aspect of the present invention is a method of enhancing mucus secretion by a mucus-secreting cell, by administering to the cell a mucus-enhancing amount of a compound that binds to an endogenous inhibitor of MARCKS protein.

A tenth aspect of the present invention is a method of screening a test compound for the ability to bind, in a mucus-secreting cell, to a site selected from (a) mucin granule membranes at the site bound by MARCKS protein, and (b) a MARCKS protein at the mucin granule membrane binding site. The method comprises administering the test compound to a mucus-secreting cell and then detecting whether the test compound inhibits binding of endogenous MARCKS protein to the mucin granule membrane.

An eleventh aspect of the present invention is a method of enhancing mucus secretion by a mucus-secreting cell, by administering to the cell a mucus enhancing amount of a compound that increases the amount of MARCKS protein in the cell, such that mucus secretion is enhanced in comparison to that which would occur in the absence of the compound.

A final aspect of the present invention is the use of a compound as described above (including proteins, peptide fragments, oligonucleotides, and non-peptide compounds) that may be used to alter mucus secretion for the preparation of a medicament for the secretion of mucus in a subject in need thereof, as described above.

BRIEF DESCRIPTION OF THE DRAWINGS

FIG. 6A is a Northern-blot and graph indicating an increase in MARCKS mRNA in cells incubated with TNF-α (lane 2 of blot, column 2 of graph) compared to cells incubated in medium alone (lane 1 of blot, column 1 of graph).

FIG. 6B is a Western-blot and graph showing a three- to four-fold increase in MARCKS protein in cells incubated with TNF-α (lane 2 of blot, column 2 of graph) as compared with cells incubated with medium only (lane 1 of blot, column 1 of graph).

FIG. 6C is a graph showing that in cells incubated with TNF-α, mucin hypersecretion was significantly augmented in response to subsequent stimulation by PMA+8-Br-cGMP or UTP when compared to mucin secretion of cells incubated in medium only. Data are presented as mean±SEM (n=6 at each point). Single asterisks (*) indicate a statistically significant difference from control (medium-only) samples (p<0.05). Single cross marks (†) indicate a statistically significant difference from stimulus (p<0.05).

DETAILED DESCRIPTION OF PREFERRED EMBODIMENTS

Figure 1B:
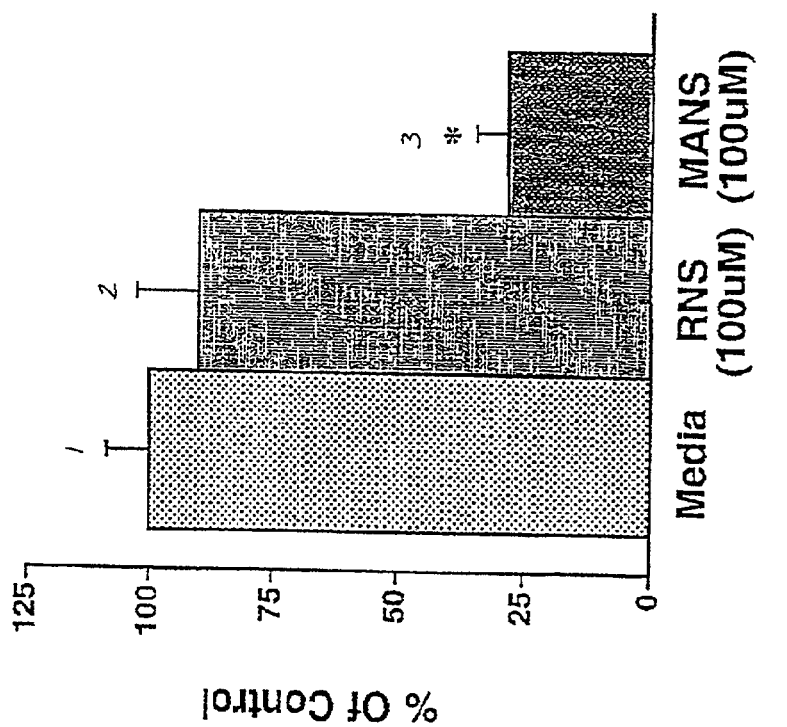
FIG. 1B graphs the inhibition of basal mucin secretion by human bronchial epithelial cells exposed to the MANS peptide (SEQ ID NO:1) or a negative control peptide consisting of the same amino acids as the MANS peptide, but in random order (RNS peptide; random N-terminal sequence). Column 1=media control; column 2=one hour incubation with 100 µM of RNS; column 3=one hour incubation with MANS peptide. The single asterisk (*) indicates that the response in column 3 was statistically different than the media control (column 1).

Mucus is the clear viscous secretion of the mucous membranes, and comprises water, mucin, lipids, and various inorganic salts. Mucin is a carbohydrate-rich glycoprotein that is secreted by specialized epithelial cells (known as goblet cells), the submaxillary glands, and other mucous glandular cells. Goblet cells are epithelial cells specialized for secretion and containing an accumulation of mucous secretory granules.

Mucous tissue (or mucosa) lines various anatomic structures in the mammalian and avian body, including the eyes, respiratory tract (alveoli, bronchi, oral cavity, larynx, nasal cavity, pharynx, trachea), gastrointestinal tract (esophagus, stomach, small and large intestine, rectum), and genitourinary tract (urethra, urinary bladder, uterus and vagina).

Alterations in the quantity of mucus secretions may be due to various underlying factors, including a change in the amount of mucous glycoproteins secreted from mucus-secreting cells, a change in the total number of mucus-secreting cells, or combinations thereof. Mediators released by the inflammatory response are known to act as mucus secretagogues, including lipid mediators, oxygen metabolites, and other cell-specific products. Larivee et al., In: *Airway Secretion*, Takishima and Shimura (Eds.), Marcel Dekker Inc., 1994, pages 469-511.

As used herein, "hypersecretion" of mucus refers to production of mucus above a normal or basal amount, or production of mucus in an amount that leads to pathological changes or symptoms.

As used herein, the "inhibiting mucus secretion" refers to a lessening or reduction in mucus secretion; it is not meant to imply the complete cessation of mucus secretion. A treatment that inhibits mucus secretion results in decreased mucus production compared to that which would occur, or would be expected, in the absence of such treatment.

Amounts of mucus secreted by a cell in culture, or by a tissue in vivo can be measured or assessed using methods as are known in the art.

As used herein, the "enhancement" or "stimulation" of mucus secretion refers to an increase in mucus secretion. A treatment that enhances mucus secretion results in increased mucus production compared to that which would occur, or would be expected, in the absence of such treatment.

As used herein, "stimulated mucus secretion" refers to mucus secretion that occurs in response to a secretagogue; this is contrasted to "basal mucus secretion" that occurs under normal physiological conditions.

As used herein, a compound that inhibits the MARCKS protein-mediated release of mucin granules (or mucus) includes those compounds that act upon a step in the MARCKS protein-mediated signaling pathway that results in mucus secretion, causing a reduction in mucus secretion.

As used herein, "endogenous" refers to compounds that are naturally occurring in a cell. Endogenous MARCKS protein thus refers to MARCKS protein that is found within a cell, as opposed to MARCKS protein introduced into that cell (either administered directly or by genetic engineering techniques).

As used herein, an "active fragment" of a MARCKS protein is one that affects (inhibits or enhances) the MARCKS protein-mediated release of mucus that occurs in response to a secretagogue such as UTP (uridine 5'-triphosphate). An active peptide fragment of MARCKS comprises an amino acid sequence that is identical or substantially identical to a contiguous sequence of amino acids found in a naturally occurring MARCKS protein. Active MARCKS protein fragments are typically at least about five, ten, fifteen, twenty or twenty-five amino acids in length, but are shorter than the complete MARCKS protein. Active MARCKS protein fragments preferably have fewer than about fifty, seventy-five, one hundred or two hundred amino acids.

A "mucus inhibitory" or "mucus inhibiting" amount of a compound is that amount which reduces or inhibits mucus secretion, compared to that which would occur in the absence of the compound. A "mucus enhancing" amount of compound is that amount which enhances or increases mucus secretion, compared to that which would occur in the absence of the compound. For example, as described herein, peptides of SEQ ID NO:2 were found to increase mucus secretion in airway epithelium in vivo when provided in a certain amount, and to inhibit mucus secretion when provided in greater amounts. The most effective amount of a particular peptide will vary depending upon the peptide, route of administration, and condition being treated. As used herein, the term "compound" is to be broadly construed to include proteins, peptide fragments, nucleotides, oligonucleotides, and other non-protein chemicals.

As used herein, a peptide inhibitor of MARCKS-related mucus secretion (or release of mucin) is a peptide that, when provided to a mucus secreting cell, inhibits or reduces the secretion of mucus compared to that which would occur in the absence of said peptide.

As used herein, a peptide enhancer of MARCKS-related mucus secretion (or mucin release) is a peptide that, when provided to a mucus secreting cell, enhances or increases the secretion of mucus compared to that which would occur in the absence of said peptide.

As used herein, "oligonucleotide" refers to DNA or RNA and can include sense and/or antisense strands as appropriate to the desired effect. Oligonucleotides useful in the present invention may be incorporated into recombinant expression vectors that include a promoter and other sequences necessary for expression of the desired translation products (such as a peptide). Alternatively, 'naked' oligonucleotides may be delivered to target cells, as is known in the art (see, e.g., Felgner et al., U.S. Pat. No. 5,580,859).

Mucosa or mucous membranes, as used herein, refers to mucosal tissues of a host wherever they may be located in the body including but not limited to respiratory passages (nasal, oral, tracheal, bronchial), genital passages (vaginal, cervical, anal and penile), urinary passages (urethra, bladder), and the eyes.

The present invention provides methods and compositions that are useful in inhibiting mucus secretion from epithelial cells. The present inventors have determined that mucin secretory processes in epithelial cells involve the protein kinase C (PKC) substrate MARCKS protein (myristolated alanine-rich C-kinase substrate). By blocking or inhibiting the function and/or production of MARCKS protein in secretory epithelial cells, mucin secretion is reduced over that which would otherwise occur (i.e., that would occur in the absence of such treatment). The present invention also provides methods and compositions that are useful in enhancing mucus secretion from epithelial cells. By enhancing the function and/or production of MARCKS protein in secretory epithelial cells, mucin secretion is increased over that which would otherwise occur (i.e., that would occur in the absence of said blocking).

The present inventors have shown that use of a fragment of the MARCKS protein reduces mucus secretion by epithelial cells. Additionally, use of antisense fragments directed against the MARCKS mRNA sequence also has been shown to decrease mucus production in epithelial cells.

Despite the previous identification of numerous mucus secretagogues, common signaling pathways and intracellular molecules involved in mucin secretion have not previously been elucidated. The present invention exploits the unexpected discovery that the myristolated alanine-rich C-kinase substrate (MARCKS) protein is involved in the secretory process of cells, and particularly in the secretion of mucus from epithelial cells (such as goblet cells). MARCKS protein is a major cellular substrate for protein kinase C (PKC), and the present inventors' studies indicate that it is a central, convergent molecule controlling release of mucin granules. While not wishing to be held to any single theory of the present invention, the MARCKS-related secretion of mucus appears to involve the interaction of mucin secretagogues with airway epithelial (goblet) cells and the activation of two separate protein kinases: PKC and PKG. Activated PKC phosphorylates MARCKS, causing its translocation from the plasma membrane to the cytoplasm, where it is targeted to the mucin granule membrane with the assistance of MARCKS-associated proteins. PKG, activated via the nitric oxide (NO)-cGMP-PKG pathway, in turn activates a cytoplasmic protein phosphatase 2A (PP2A), which dephosphorylates MARCKS, stabilizing its attachment to the granule membrane and allowing MARCKS to cross-link actin filaments, thereby tethering the granule to the cytoskeleton for movement and exocytosis. This proposed signaling pathway is generally depicted in FIG. 4.

The present inventors identified MARCKS mRNA and protein in human bronchial epithelial cells, and both mRNA and protein levels increased with secretory cell differentiation in vitro. The MARCKS in these cells was phosphorylated by the phorbol ester PMA (phorbol 12-myristate 13-acetate), while subsequent addition of a cGMP activator (8-bromo-cGMP), caused dephosphorylation. Mucin secretion provoked (i.e., stimulated) by the pathophysiologically relevant secretagogue uridine triphosphate (UTP) (or by a combination of PMA and 8-bromo-cGMP) was inhibited in a dose-dependent manner by a myristoylated peptide fragment of the N-terminal region of MARCKS protein (the proposed site of the protein's attachment to granule membranes). Accordingly, this myristoylated peptide fragment of the N-terminal region of MARCKS protein, as well as other active peptide fragments, are useful in methods of inhibiting mucus secretion. As described further herein, the administration of certain active fragments of MARCKS protein has been found to be capable of both increasing and decreasing mucus secretion by epithelial mucus-secreting cells.

The present inventors have discovered that antisense oligonucleotides directed against MARCKS protein block or inhibit mucin secretion, as described further herein. Accordingly, such antisense oligonucleotides find use in methods of inhibiting mucus secretion.

Figure 4:
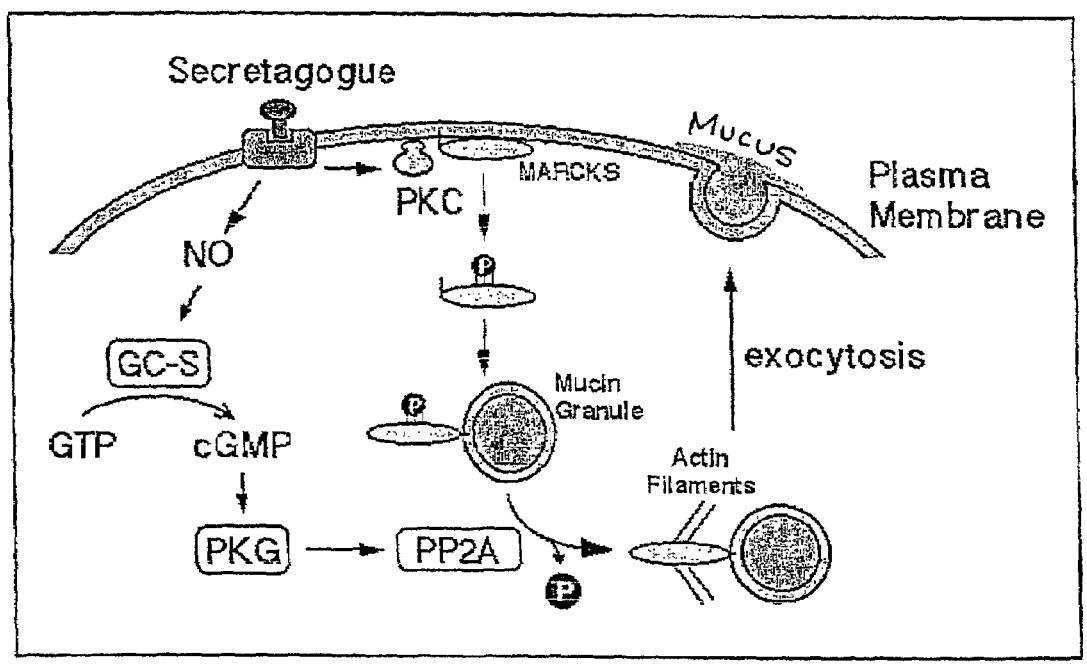
FIG. 4 is an illustration of a proposed signaling pathway of MARCKS-mediated mucin secretion by human epithelial cells. In this Figure, PKC=protein kinase C; PKG=cGMP-dependent protein kinase; GC-S=soluble guanylyl cyclase; PP2A=protein phosphatase 2A; NO=nitric oxide; GTP=guanosine triphosphate; and cGMP=cyclic guanosine monophosphate. In this proposed pathway, mucin secretagogues (shown in the Figure as binding to a receptor) interact with airway epithelial (goblet) cells and activate two separate protein kinases: PKC and PKG. Activated PKC phosphorylates MARCKS, causing its translocation from the plasma membrane to the cytoplasm, where it is targeted to the mucin granule membrane with the assistance of MARCKS-associated proteins. PKG, activated via the nitric oxide (NO)-cGMP-PKG pathway, in turn activates a cytoplasmic protein phosphatase 2A (PP2A), which dephosphorylates MARCKS, thus stabilizing its attachment to the granule membrane and allowing MARCKS to cross-link actin filaments. This tethers the granule to the cytoskeleton for movement and exocytosis.

Additionally, certain non-protein inhibitors of components in the mucus secretion signaling pathway illustrated in FIG. 4 inhibit mucus secretion in mucus-secreting cells, and are thus useful in the practice of methods the present invention. For example, inhibitors of PKC such as calphostin C, inhibitors of cyclic GMP such as Rp-8-Br-PET-cGMP, inhibitors of PKG such as Rp-8-Br-PET-cGMP, inhibitors of soluble guanylyl cyclase such as LY83585 and inhibitors of phosphatase such as okadaic acid each inhibit mucin secretion in cells stimulated by the above-listed secretagogues. Accordingly, such inhibitors of components of the mucin secretion signaling pathway find use in methods of inhibiting mucus secretion.

Other compounds that find use in the practice of the present invention are those compounds that increase the amount (i.e., the concentration) of MARCKS protein in a mucus secreting cell. Such compounds have been found to increase mucus secretion in these cells. Although the mechanisms of how these compounds increase the level or amount of MARCKS protein in the cell are not known, possible mechanisms include (1) transcriptional modulation of the production of MARCKS mRNA (i.e., through binding or alteration of transcription factors, or other mechanisms of modulating transcription) by these compounds, directly or indirectly, and (2) translational control or modulation of the expression of MARCKS protein (e.g., by binding in the upstream regulatory region of the MARCKS mRNA, thus potentially altering secondary structure that inhibits the amount of MARCKS protein expressed) by these compounds, either directly or indirectly. As used herein, compounds that increase the amount of MARCKS protein in a mucus secreting cells may be proteins, peptides, or non-protein compounds. In one embodiment of the invention, the compound is bacterial lipopolysaccharide (LPS). Preferably, the compound is a protein or peptide. In a particularly preferred embodiment of the invention, the compound is a cytokine. In a more particularly preferred embodiment of the invention, the compound that increases the amount of MARCKS protein in a mucus secreting cell is the cytokine Tumor Necrosis Factor-alpha (TNF-α).

The present invention thus provides methods and compositions useful in regulating (increasing or decreasing) mucus secretion. Such methods and compositions are useful in the treatment of medical conditions in which mucus hypersecretion occurs, and are particularly useful in the respiratory tract. Methods and compositions of the present invention may further be useful in treating medical conditions in which it is desired to increase mucus secretion.

The methods and compositions of the present invention may be used to inhibit or reduce mucus secretion occurring from any mucus-secreting cell (such as goblet cells) or tissue (such as mucous membranes of the airways). While not wishing to be held to a particular theory, the present inventors also believe that the compounds and methods of the present invention may also be used to block the secretion of inflammatory mediators from cells such as macrophages, neutrophils and mast cells. In this way, the present mucus-inhibitory compounds may have a dual function of decreasing mucus secretion and inflammation.

As discussed below, the present invention is also directed to active peptide fragments of MARCKS protein that exhibit a bimodal effect when delivered to mucus-secreting cells. At a certain dose level (a mucus-enhancing amount), such peptides increase or enhance mucus secretion (compared to that which would occur in the absence of such treatment). At a different dose level, this enhancement is no longer observed. An even more extreme dose results in the inhibition of or decrease in mucus secretion (compared to that which would occur in the absence of such treatment).

Accordingly, the present invention provides methods and compositions for regulating mucus secretion, by regulating the effects of MARCKS protein in the mucus-secretory pathway. Such regulation can be achieved by administering active fragments of MARCKS protein in pre-determined amounts, administration of mucus-inhibiting amounts of MARCKS antisense oligonucleotides, or administration of these or other compounds (alone or in combination) that enhance or inhibit the MARCKS-related secretory pathway. Such compounds include those that block the dephosphorylated MARCKS protein binding event that leads to mucin release. Such compounds may bind to and block the site that is bound by endogenous MARCKS protein, or may bind to the MARCKS protein at the pertinent site. The MANS peptide described herein is believed to compete with endogenous MARCKS protein for the pertinent binding site in the cell, thus blocking the MARCKS-mediated release of mucin within the cell. Alternatively, an antibody directed to the N-terminal sequence of the MARCKS protein (e.g., the MANS sequence) would be predicted to bind to endogenous MARCKS protein and block binding.

While not wishing to be held to a single theory underlying the present invention, it is believed that compounds that increase MARCKS-related mucus secretion when administered to a mucus-secreting cell (such as the MA-PSD peptide; SEQ ID NO:2) may be binding to endogenous proteins in the cell that would otherwise bind to MARCKS protein and inhibit MARCKS from completing a step in the mucus-secretion pathway. Calmodulin is one such endogenous inhibitor of MARCKS; calmodulin binds to MARCKS and prevents phosphorylation, thus preventing the MARCKS protein from disengaging from the plasma membrane. As used herein, "endogenous inhibitors of MARCKS protein" are compounds naturally present in a cell that bind to MARCKS protein and prevent the completion of a step in the MARCKS-related mucus secretion pathway. A peptide or other compound that binds to a MARCKS inhibitor would leave more endogenous MARCKS protein free to function in the mucus secretion pathway. Thus, a method for increasing mucus secretion is to administer to a mucus-secreting cell, a compound that binds to a MARCKS protein inhibitor.

It will be desirable, in many therapeutic situations, to maintain some level of mucus secretion (i.e., a basal or normal level), for the protective effects of mucus. Maintenance of basal mucus secretion may be achieved by regulating the dose of the active compound utilized. Additionally, while not wishing to be held to a single theory of the invention, the present inventors suggest that in some mucous membranes, a basal level of mucus secretion may be maintained by a pathway separate from the MARCKS-related pathway and stimulated mucus secretion.

The present invention provides methods and compositions able to decrease or reduce mucus hypersecretion that occurs in many pathological conditions, including pathological conditions related to inflammatory, viral, bacterial, or genetic causes. In particular, the present methods and compositions provide methods of treating airway diseases in which mucus secretion is increased over that which occurs in the absence of the disease (i.e., is increased over basal levels, or over normally-occurring levels of mucus secretion). Subjects to be treated by the present methods include human and non-human subjects. Non-human subjects include companion animals such as cats and dogs, as well as livestock such as cattle, horses, sheep and swine.

The present methods and compositions may be used to reduce mucus secretion, or to inhibit mucus hypersecretion, in any secretory epithelium, or epithelial cell, including but not limited to airway epithelial cells (e.g., oral, nasal, bronchial), ocular epithelial cells, gastric or intestinal epithelial cells, and epithelial cells lining the reproductive tract (e.g., vaginal, cervical). As will be apparent to those skilled in the art based on the subject and the condition being treated, it may be desirable to maintain a basal level of mucus secretion, while reducing hypersecretion of mucus. As used herein, a treatment that reduces or inhibits mucus secretion refers to a treatment that reduces the amount of secreted mucus compared to that which would occur in the subject in the absence of such treatment.

The present invention also provides a method and compositions for increasing or stimulating mucus secretion by epithelial cells, including but not limited to airway epithelial cells, ocular epithelial cells (corneal epithelium or conjunctiva), gastric or intestinal epithelial cells, and epithelial cells lining the reproductive tract. As used herein, a treatment that increases, enhances or stimulates mucus secretion refers to a treatment that increases the amount of secreted mucus compared to that which would occur in the absence of such treatment. In particular, the present methods and compositions are useful in increasing the secretion of mucus by ocular epithelial cells (to treat dry-eye conditions), and by vaginal epithelial cells (to treat vaginal dryness).

Figure 1A:
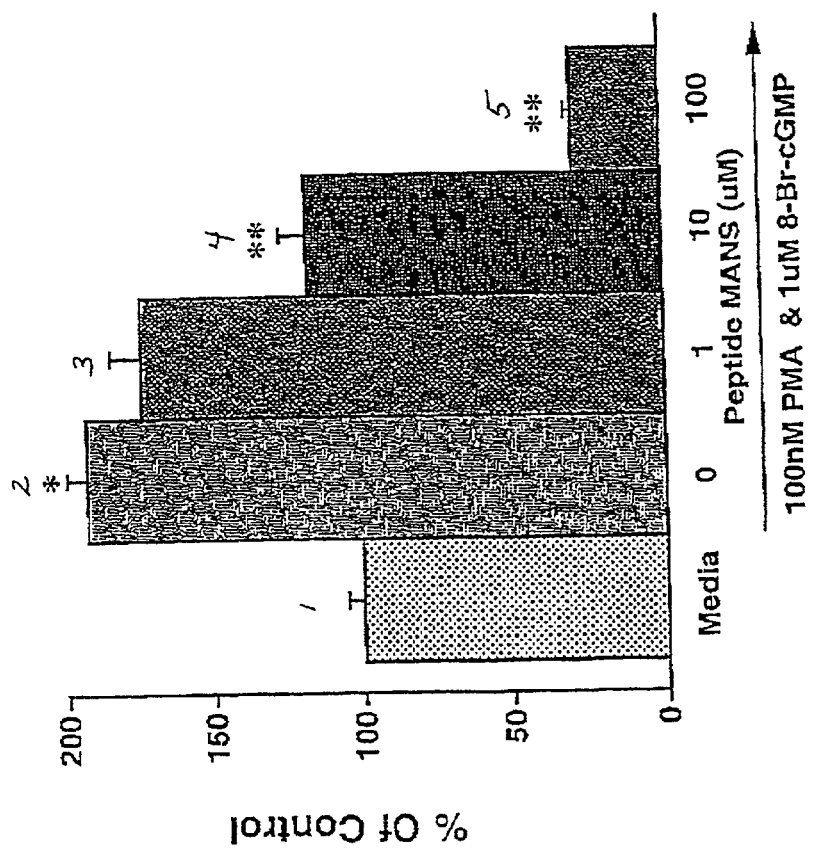
FIG. 1A is a graph of stimulated mucin secretion by human bronchial epithelial cells in vitro in response to varying amounts of the MANS peptide (SEQ ID NO:1). Column 1=media/control (no peptide, no stimulation); column 2=100 nM PMA and 1 µM 8-Br-cGMP (stimulated secretion); column 3=1 µM MANS peptide, 100 nM PMA and 1 µM 8-Br-cGMP; column 4=10 µM MANS peptide, 100 nM PMA and 1 µM 8-Br-cGMP; and column 5=100 µM MANS peptide, 100 nM PMA and 1 µM 8-Br-cGMP. Single asterisks (*) indicate that the measured response was statistically different than the media control (column 1), and double asterisks (**) indicate that the response was statistically different than that of stimulated cells that were not exposed to the MANS peptide (column 2).
Figure 2:
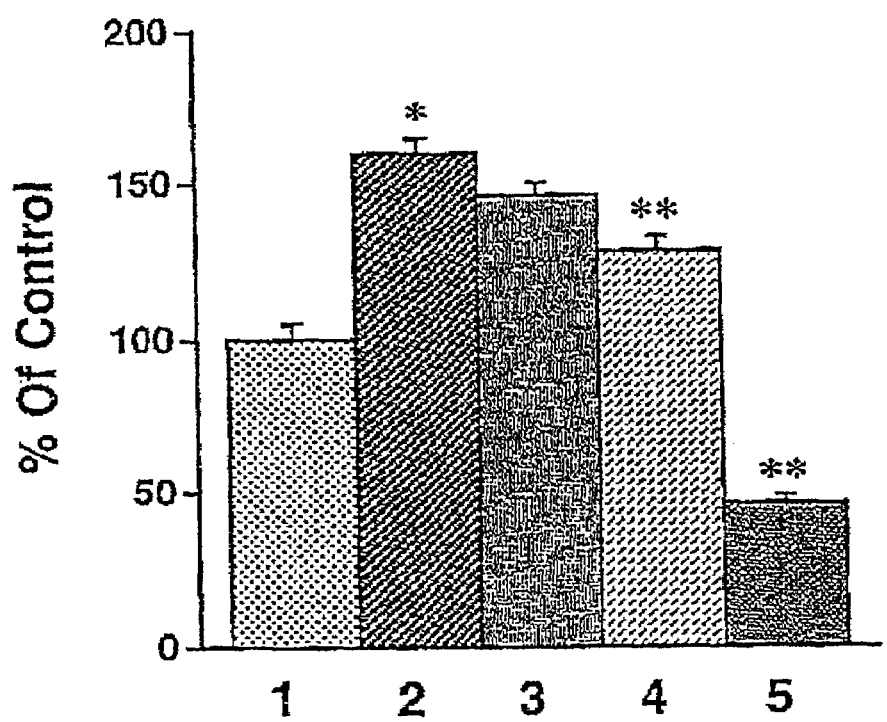
FIG. 2 is a graph of the effects of varying amounts of the MANS peptide (SEQ ID NO:1) on UTP-induced mucin secretion by human bronchial epithelial cells in vitro. Column 1 is the media/control; column 2=0.1 mM UTP; column 3 =0.1 mM UTP and 1 µM MANS peptide; column 4=0.1 mM UTP and 10 µM MANS peptide; and column 5=0.1 mM UTP and 100 µM MANS peptide. Single asterisks (*) indicate that the measured response was statistically different than the media control (column 1), and double asterisks (**) indicate that the response was statistically different than that of UTP-stimulated cells that were not exposed to the MANS peptide (column 2).

The peptides and compounds of the present invention block mucus secretion in response to known activators of PKC and protein kinase G (FIG. 1), and to physiologically relevant stimuli (e.g., UTP). (FIG. 2)

The present invention thus provides methods and compositions for treating epithelial cells or epithelial tissue, where it is desirable to decrease the amount of mucus secreted by the cells or tissue. The present invention also thus provides methods and compositions for treating epithelial cells or epithelial tissue, where it is desirable to increase the amount of mucus secreted by the cells or tissue. In particular the present invention provides methods and compositions for treating respiratory conditions where it is desirable to decrease the amount of mucus present in the airways, or where it is desirable to increase the amount of mucus present in the airways. Conditions suitable for treatment by the present methods include human and animal inflammatory, viral or bacterial airway disease (e.g., asthma, chronic obstructive pulmonary disease, common cold, rhinitis, acute or chronic bronchitis, pneumonia, and kennel cough), allergic conditions (atopy, allergic inflammation), bronchiectasis, and certain genetic conditions (e.g., cystic fibrosis).

Mucus Secretion in the Airways

Normal mucus secretion in the lung plays an important role in clearing inhaled foreign particles and pathogens from the airways. Mucus traps inhaled particles, and is then removed from the airways by ciliary action or by coughing. Above-normal levels of mucus secretion (hypersecretion) in the airways can lead to intraluminal mucus accumulation, resulting in airflow obstruction and an increased susceptibility to infectious agents. Secretory cells in the airways include submucosal glands and superficial epithelial mucus cells (goblet cells).

Airway mucus secretion is an important determinant in the prognosis and clinical features of pulmonary diseases. Hypertrophy and/or hyperplasia of airway secretory cells (bronchial glands and epithelial goblet cells) are often found in conditions associated with chronic airway inflammation. In subjects with chronic bronchitis and bronchial asthma, goblet cell hyperplasia has been observed, with a two- to three-fold increase in the numbers of goblet cells compared to controls. Cutz et al., *Histopathology* 2:407-421 (1978), Glynn & Michaels *Thorax* 15:142-153 (1960). Inflammation of the airways may induce mucus hypersecretion by multiple mechanisms, including the release of chemical mediators from surrounding tissues and cells. Airway mucus hypersecretion is a particularly dominant clinical finding in cystic fibrosis, bronchitis, chronic obstructive pulmonary disease (COPD), emphysema, and bronchial asthma. See, e.g., *Airway Secretion*, Takishima and Shimura (Eds.), Marcel Dekker Inc., 1994. The presence of excessive bronchial mucus can lead to respiratory failure and bacterial infection. Lungs of asthmatic patients, at autopsy, often show the presence of excessive bronchial mucus and mucus plugging. Methods of reducing airway mucus secretion would be useful for the treatment of such conditions, as well as in treating bacterial or viral infections (e.g., pneumonia, influenza, and the common cold); in animals, such methods are further useful in treating kennel cough and equine COPD.

Various methods are currently in use to reduce mucus secretion when needed in disease states. Some therapies act to decrease the signals or stimuli that upregulate mucus secretion. For example, inflammatory mediators may upregulate mucus secretion; steroid treatments are often used to decrease inflammation and thus indirectly decrease mucus secretion. Antihistamines are used to block the responses to allergens which can trigger attacks of allergic asthma. The thickened mucus present in patients with cystic fibrosis is removed by compression therapy, and infections occurring due to the thickened mucus are treated with antibiotics. The methods and compounds of the present invention vary from the above treatments in that cellular secretion of mucus in response to a variety of stimuli is directly blocked at the cellular level.

Ocular Mucus Layer

The mucus layer on the ocular surface is important in maintaining and spreading the tear film, and is required for normal functioning of the eyes. The ocular surface epithelia has been shown to express multiple mucin genes. Gipson, *Adv. Exp. Med. Biol.* 438:221 (1998). Various diseases and syndromes result in pathological "dry-eye" conditions, including keratoconjunctivitis sicca, Stevens-Johnson syndrome, ocular pemphigoid, and surgery- or radiation-induced dry-eye. The ocular surface epithelia in such diseases undergoes changes, which may include loss of goblet cells, mucin deficiency, and keratinization. Lower goblet cell densities in the ocular epithelia have been demonstrated in these syndromes. Ralph, *Invest. Ophthalmol.* 14:299 (1975).

In addition to subjects in which dry-eye causes discomfort in daily life, many individuals have "marginal" dry-eye which may only present difficulties when the subject attempts to wear contact lenses. Contact lens intolerance is frequently due to insufficient tear film. Jurkus et al., *J. Am. Optom. Assoc.* 65:756 (1994); Toda et al., *Br. J. Ophthal.* 80:604 (1996). Existing treatments for dry-eye include topical use of tretinoin (Tseng, *J. Am. Acad. Dermatol.* 15:860 (1986)) or retinoic acid (Driot & Bonne, *Invest. Ophthalmol.* 33:190 (1992)).

Increasing mucus secretion in the eyes is desirable where a lack of ocular mucus affects the normal function of the eye. Additionally, increasing mucus secretion in the eye is desirable as an aid in wearing contact lenses.

Administration

The method of the present invention can be used to reduce (i.e., decrease or inhibit) or to enhance (i.e., increase or stimulate) the production of mucus secretions by mucous membranes or mucus-secreting cells, in a subject in need of such treatment for any reason. Using methods of administration as are known in the art, the present therapies can be directed to the mucous membranes or mucus-secreting cells of a particular target organ (including but not limited to the oral cavity, nasal cavity, lungs, gastrointestinal tract, eye and reproductive tract), in order to reduce or increase the amount of mucus secreted by, or retained upon, the surfaces being treated. The change (reduction or increase) in mucus is assessed by comparison to that which was present prior to treatment (or in the absence of treatment), or to that which would be expected in the absence of such treatment in view of the subject's condition.

The methods of the present invention may be used in conjunction with other therapies or compounds, including steps to remove retained mucus secretions from the airways of subjects prior to the step of administering the present compounds. This facilitates application of the active agent to the respiratory epithelia during the administering step. Such removal of retained mucus secretions can be carried out by any suitable physical or medicinal means as are known in the art.

Mucosal delivery of peptide-based drugs is discussed in Chien, Novel Drug Delivery Systems, Chapter 4 (Marcel Dekker, 1992); nasal drug delivery is discussed in Chien, supra, in Chapter 5. See also Chang et al., Nasal Drug Delivery, "Treatise on controlled Drug Delivery", Chapter 9 (Marcel Dekker, 1992). Agents known to enhance absorption of drugs through the skin are described in Sloan, Chapter 5, "Prodrugs: Topical and Ocular Drug Delivery" (Marcel Dekker, 1992). The peptides of the present invention can be administered into target cells directly, for example using liposomes. It is expected that those skilled in the art may adapt such techniques and other known drug delivery techniques for use with the compounds of the present invention without undue experimentation.

Pharmaceutical compositions for use in the present method of treatment include those suitable for inhalation, oral, rectal, vaginal, topical (including buccal, dermal and ocular) administration. The compositions may be prepared by any of the methods well known in the art. The most suitable route of administration in any case will depend upon the location of the tissue to be treated, the nature and severity of the condition being treated, and the particular active compound which is being used, as will be apparent to those skilled in the art. The dosage of active compound for treatment of diseases of the respiratory tract will vary depending on the condition being treated and the state of the subject. One skilled in the art would be able to determine appropriate dosages of specific compounds without undue experimentation, using dose response studies as are known in the art.

The active compounds disclosed herein may be administered to the airways of a subject by any suitable means, but are preferably administered by generating an aerosol comprised of respirable particles, the respirable particles comprised of the active compound, which particles the subject inhales. The respirable particles may be liquid or solid. The particles may optionally contain other therapeutic ingredients. (See, e.g., U.S. Pat. No. 5,849,706 to Molina y Vedia et al.)

In methods of treating the bronchi and/or alveoli, particles comprised of active compound for practicing the present invention should include particles of respirable size: that is, particles of a size sufficiently small to pass through the mouth and larynx upon inhalation and into the bronchi and alveoli of the lungs. In general, particles ranging from about 0.5 to 10 microns in size (more particularly, less than about 5 microns in size) are respirable. Particles of non-respirable size which are included in the aerosol tend to deposit in the throat and be swallowed, and the quantity of non-respirable particles in aerosols intended for treatment of the alveoli and/or bronchi is preferably minimized. For nasal administration, a particle size in the range of 10-500 microns is preferred to ensure retention in the nasal cavity.

Liquid pharmaceutical compositions of active compound for producing an aerosol can be prepared by combining the active compound with a suitable vehicle, such as sterile pyrogen free water.

Administration of the active compounds may be carried out therapeutically or prophylactically (e.g., before substantial lung blockage due to retained mucus secretions has occurred, or at a time when such retained secretions have been at least in part removed, as discussed above.)

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers consist of the active ingredient in a liquid carrier, typically water or a dilute aqueous alcoholic solution, and preferably made isotonic with body fluids.

Aerosols of solid particles comprising the active compound may likewise be produced with any solid particulate medicament aerosol generator. One illustrative type of solid particulate aerosol generator is an insufflator.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). Formulations for oral administration may optionally include enteric coatings known in the art to prevent degradation of the formulation in the stomach and provide release of the drug in the small intestine.

Formulations suitable for rectal or vaginal administration may be presented as unit dose suppositories. These may be prepared by admixing the active compound with one or more conventional solid carriers, for example, cocoa butter, and then shaping the resulting mixture.

Formulations suitable for topical application to the eye, mouth, nasal or other surfaces may take the form of an ointment, cream, lotion, paste, gel, spray, aerosol, or oil.

Peptides

The myristoylated alanine-rich C kinase substrate (MARCKS) protein is a major cellular substrate for protein kinase C. MARCKS is regulated in a cell-, tissue- and developmental stage-specific manner, and expression of MARCKS can be stimulated by various cytokines. MARCKS has been identified in human, bovine, rodent and avian species. Harlan et al., *J. Biol. Chem.* 266:14399 (1991); Graff et al., *J. Biol. Chem.* 266:14390 (1991); Graff et al., *Mol. Endocrinol.* 3:1903 (1989); Stumpo et al., *Proc. Natl. Acad. Sci. USA* 86:4012-16 (June 1989).

Peptides corresponding to the MARCKS protein are commercially available. A MARCKS "psd peptide" is available from BIOMOL (Plymouth Meeting, Pa.), having the sequence KKKKKRFSFK KSFKLSGFSF KKNKK (SEQ ID NO:2). See P. Blackshear, *J. Biol. Chem.* 268:1501 (1993).

The present inventors have identified two specific active fragments of MARCKS protein that are able to affect mucus secretion. A myristoylated polypeptide, 24 amino acids in length, with sequence Myristic acid-GAQFSK-TAAKGEAAAERPGEAAVA (SEQ ID NO:1), is referred to herein as the MANS peptide for myristolated N-terminal sequence. The peptide inhibits secretion of mucus from mucous membranes and mucus-secreting cells, including human airway epithelial cells. The present inventors' data suggests that this peptide blocks the attachment of MARCKS protein to the mucin granule, thus blocking or inhibiting the release of mucin granules and the secretion of mucus by the cell.

Figure 3A:
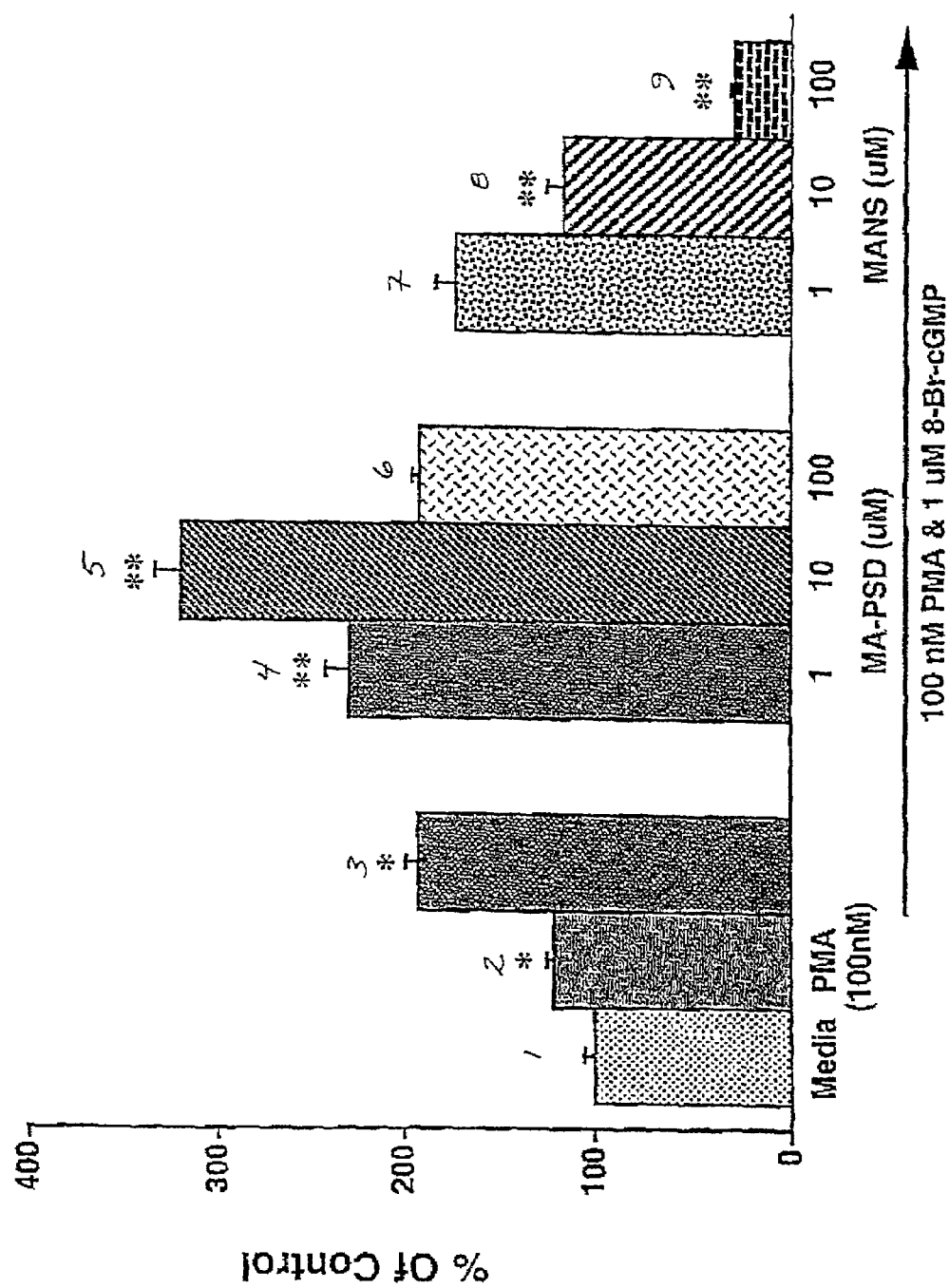
FIG. 3A is a graph of the effects of the MANS peptide (SEQ ID NO:1) and the MA-PSD peptide (SEQ ID NO:2) on stimulated mucin secretion by human bronchial epithelial cells in vitro. Column 1=media/control; column 2=100 nM PMA; column 3=100 nM PMA and 1 µM 8-Br-cGMP; column 4=100 nM PMA, 1 µM 8-Br-cGMP and 1 µM M-PSD peptide; column 5=100 nM PMA, 1 µM 8-Br-cGMP and 10 µM MA-PSD peptide; column 6=100 nM PMA, 1 µM 8-Br-cGMP and 100 µM MA-PSD peptide; column 7=100 nM PMA, 1 µM 8-Br-cGMP and 1 µM MANS peptide; column 8=100 nM PMA, 1 µM 8-Br-cGMP and 10 µM MANS peptide; and column 9=100 nM PMA, 1 µM 8-Br-cGMP and 100 µM MANS peptide. Single asterisks (*) indicate that the response was statistically different than the media control (column 1), and double asterisks (**) indicate that the response was statistically different than that in stimulated cells that were not exposed to the MANS peptide (column 3).
Figure 3B:
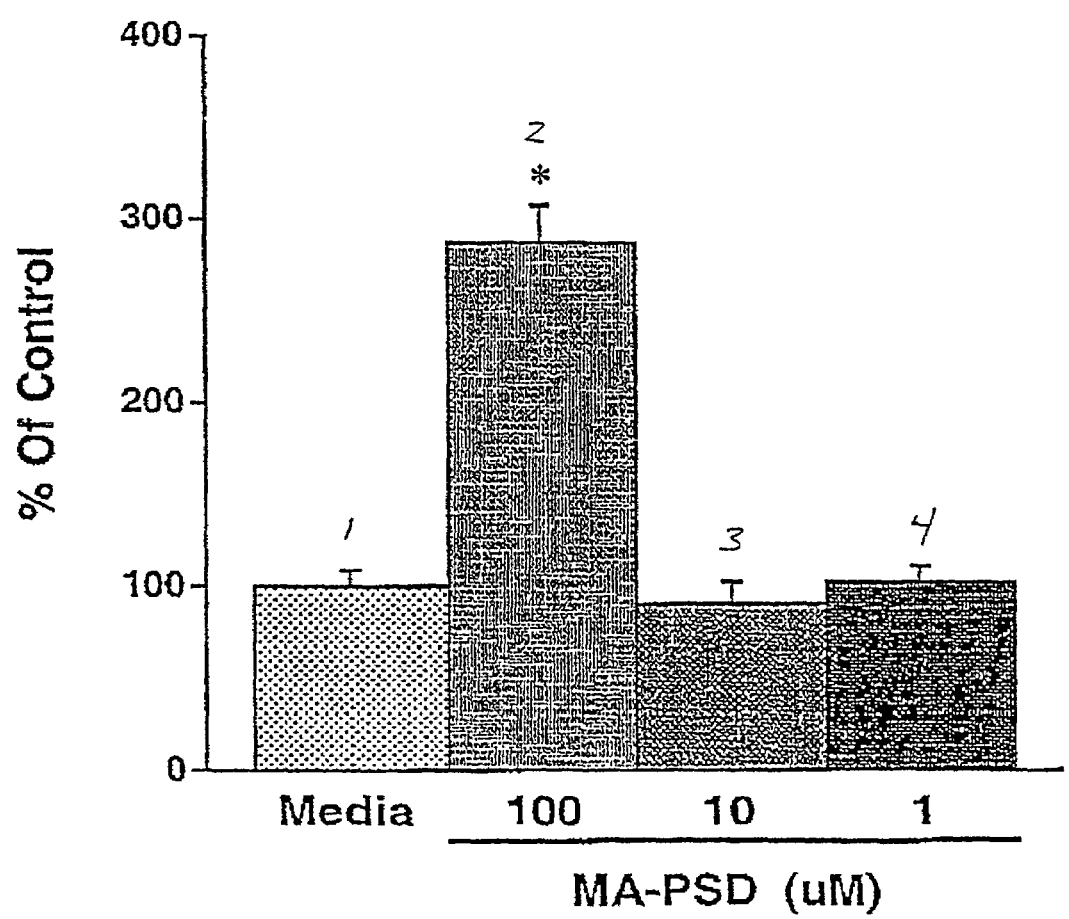
FIG. 3B graphs the effect of one hour of incubation with the MA-PSD peptide (SEQ ID NO:2) on basal mucin secretion by human bronchial epithelial cells in vitro. Column 1=media/control; column 2=100 µM MA-PSD; column 3=10 µM MA-PSD; column 4=1 µM MA-PSD. The single asterisk (*) indicates that the response in column 3 was statistically different than the media control (column 1).

A second peptide corresponding to the PSD (phosphorylation) site of MARCKS was also tested. At some concentrations this peptide stimulates mucus secretion, while at other doses (higher) it has no effect on stimulated secretion (FIG. 3), and it is predicted that even higher doses will decrease stimulated mucus secretion. The PSD peptide sequence is myristic acid-KKKKKRFSFKKSFKLSGFS-FKKNKK (SEQ ID NO:2), referred to herein as the MA-PSD peptide. While not wishing to be held to a single theory underlying the present invention, the inventors believe that MARCKS protein fragments that are able to increase mucus secretion (such as the MA-PSD peptide, SEQ ID NO:2) may be binding to endogenous proteins in the cell that competitively inhibit the phosphorylation of MARCKS, thus inhibiting the release of MARCKS from the plasma membrane into the cell interior (see FIG. 4). One such inhibitor of MARCKS phosphorylation is calmodulin. Other "MARCKS inhibitors", for purposes of the present invention, are those endogenous compounds that prevent the MARCKS protein from completing a necessary step in the mucus-secretion pathway. MARCKS inhibitors may thus act to inhibit the phosphorylation or the dephosphorylation of MARCKS (each of which is necessary in the present pathway), or bind to MARCKS to prevent its binding to the mucin granule membrane. Compounds of the present invention that increase the secretion of mucus may be acting by binding to such endogenous inhibitors, thus freeing endogenous MARCKS protein to complete the mucus-secretion pathway.

Thus, peptide fragments of the MARCKS protein may be designed, tested and selected for their ability to inhibit or enhance mucus secretion, using the present disclosure and methods known in the art.

The nucleotide and amino acid sequences of human MARCKS cDNA and protein as reported by Harlan et al., *J. Biol. Chem.* 266:14399 (1991) (GenBank Accession No. M68956) are provided as SEQ ID NO:3 and SEQ ID NO:4. The nucleotide and amino acid sequences of human MARCKS cDNA and protein as reported by Sakai et al., *Genomics* 14:175 (1992) are provided as SEQ ID NO:5 and SEQ ID NO:6. An additional publication (Harlan et al., *J. Biol. Chem.* 266(22):14399 (1991) provides a nucleotide sequence for human MARCKS that differs from that of Sakai et al. at nucleotides 619 and 724; in this sequence, G is substituted for T at position 619 and C is substituted for G at position 724. Additional allelic variants of human and other MARCKS proteins would be expected.

While not wishing to be held to a single theory underlying the present invention, the present inventors propose that the pathway for the involvement of MARCKS in mucus secretion in airway epithelium is as shown in FIG. 4. It is currently believed that active peptide fragments of MARCKS affect mucus secretion at the level of the interaction of MARCKS with the mucin granules, which contain the major protein components of mucus. As shown in FIG. 4, the present inventors believe that MARCKS must be dephosphorylated to bind to the mucin granule, which triggers mucin exocytosis and results in mucus secretion.

The methods of the present invention include the use of isolated DNA molecules encoding the peptides of the present invention. Such isolated DNA molecules are useful in producing the therapeutic peptides, and may additionally be used in an appropriate gene expression vector for gene therapy, using methods as are known in the art for the expression of the peptide in vivo. Cell-specific or inducible promoters may further be used to control the expression of the therapeutic peptide in vivo. Methods of delivering DNA encoding a desired peptide to achieve a therapeutic effect is disclosed, e.g. in U.S. Pat. Nos. 5,580,859 and 5,703,055 to Felgner et al.

Analogs of the therapeutic peptides disclosed herein are an aspect of the present invention. As used herein, an "analog" is a chemical compound similar in structure to a first compound, and having a similar physiologic action as the first compound. With particular reference to the present invention, MARCKS peptide analogs are those compounds which, while not having the exact amino acid sequences of the native MARCKS fragment, are capable of binding to the same sites as the native MARCKS fragment. Such analogs may be peptide or non-peptide analogs, including nucleic acid analogs, as described in further detail below.

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the p20 ligands may be designed and synthesized in accordance with known techniques.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. patent references cited herein be incorporated by reference herein in their entirety). See also Waldrop, *Science,* 247, 28029 (1990); Rossmann, *Nature,* 333, 392-393 (1988); Weis et al., *Nature,* 333, 426-431 (1988); James et al., *Science,* 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Tie, preferably Ala or Leu; Leu may be replaced with Ala, Val or lie, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His; Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules which bind to sites bound by the native MARCKS fragments disclosed herein. See, e.g., Knight, *BIO/Technology*, 8, 105 (1990). Itzstein et al, *Nature*, 363, 418 (1993); Lam et al, *Science*, 263, 380 (January 1994) (rational design of bioavailable nonpeptide cyclic ureas that function as HIV protease inhibitors). Analogs may also be developed by generating a library of molecules, selecting for those molecules which act as ligands for a specified target, and identifying and amplifying the selected ligands. See, e.g., Kohl et al., *Science*, 260, 1934 (1993). Techniques for constructing and screening combinatorial libraries of oligomeric biomolecules to identify those that specifically bind to a given receptor protein are known. Suitable oligomers include peptides, oligonucleotides, carbohydrates, non-oligonucleotides (e.g., phosphorothioate oligonucleotides; see *Chem. and Engineering News*, page 20, 7 Feb. 1994) and nonpeptide polymers (see, e.g., "peptoids" of Simon et al., *Proc. Natl. Acad. Sd. USA*, 89, 9367 (1992)). See also U.S. Pat. No. 5,270,170 to Schatz; Scott and Smith, *Science*, 249, 386-390 (1990); Devlin et al., *Science* 249, 404-406 (1990); Edgington, *BIO/Technology*, 11, 285 (1993). Peptide libraries may be synthesized on solid supports, or expressed on the surface of bacteriophage viruses (phage display libraries). Known screening methods may be used by those skilled in the art to screen combinatorial libraries to identify suitable peptide analogs. Techniques are known in the art for screening synthesized molecules to select those with the desired activity, and for labelling the members of the library so that selected active molecules may be identified. See, e.g., Brenner and Lerner, *Proc. Natl. Acad. Sci. USA*, 89, 5381 (1992); PCT U593/06948 to Berger et al.; Simon et al., *Proc. Natl. Acad. Sci. USA*, 89, 9367, (1992); U.S. Pat. No. 5,283,173 to Fields et al.

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology*, 11, 285 (1993). U.S. Pat. No. 5,270,163 to Gold and Tuerk describes a method for identifying nucleic acid ligands for a given target molecule by selecting, from a library of RNA molecules with randomized sequences, those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA*, 89, 8864 (1992) and Tsai and Keene, *J. Immunology*, 150, 1137 (1993).

Antisense Oligonucleotides

The present inventors have further demonstrated that antisense oligonucleotides directed against MARCKS mRNA decreases (inhibits) mucus secretion in human airway epithelial cells. (See Example 6 and FIG. 5).

It has been demonstrated that antisense oligonucleotides that are complementary to specific RNAs can inhibit the expression of cellular genes as proteins. See Erickson and Izant, Gene Regulation: Biology Of Antisense RNA And DNA, Vol. 1, Raven Press, New York, 1992. For example, selective inhibition of a p21 gene that differed from a normal gene by a single nucleotide has been reported. Chang et al., *Biochemistry* 1991, 30:8283-8286. Many hypotheses have been proposed to explain the mechanisms by which antisense oligonucleotides inhibit gene expression, however, the specific mechanism involved may depend on the cell type studied, the RNA targeted, the specific site on the RNA targeted, and the chemical nature of the oligonucleotide. Chiang et al., *J. Biol. Chem.* 1991, 266:18162-18171; Stein and Cohen, *Cancer Res.* 1988, 48:2659-2668.

The present invention provides oligonucleotides substantially complementary to a MARCKS protein nucleotide sequence that occurs endogenously in a mucus-secreting cell. Such oligonucleotides are useful in decreasing mucus production by cells into which they are delivered. "Nucleotide sequence" refers to a polynucleotide formed from a series of joined nucleotide units. The term "substantially complementary", as used herein, refers to that amount of sequence complementarity between the oligonucleotide and a MARCKS gene nucleotide sequence which allows for interstrand hybridization under physiological conditions and enables the oligonucleotide to inhibit the expression of the MARCKS gene. Interstrand hybridization is the interaction between the oligonucleotide and the MARCKS nucleotide sequence. The potential of forming a stable interstrand hybrid can be determined by those skilled in the art using methods known in the art, such as, for example, determination of the melting temperature for the hybrid by mathematical modeling or empirical analysis, or solid support nucleic acid hybridizations. (See, e.g., Marmur and Doty, *J. Mol. Biol.* 1962, 5, 113).

Antisense DNAs used in the present invention are able to produce the corresponding antisense RNAs. An antisense RNA molecule has the nucleotide bases in the reverse or opposite order for expression. Such antisense RNAs are well known in the art, see e.g., U.S. Pat. No. 4,801,540 to Calgene Inc.

As used herein, the term "MARCKS nucleotide sequence" refers to any nucleotide sequence derived from a gene encoding a MARCKS protein, including, for example, DNA or RNA sequence, DNA sequence of the gene, any transcribed RNA sequence, RNA sequence of the pre-mRNA or mRNA transcript, and DNA or RNA bound to protein.

Oligonucleotides targeted to sequences in MARCKS genes can be used to inhibit mucus production in epithelial cells. The oligonucleotide may be any length of sequence capable of forming a stable hybrid with the endogenous MARCKS nucleotide sequence under physiologic conditions. It is preferred that the length of the oligonucleotide be between 5 and 200 nucleotides. It is more preferred that the oligonucleotide be between 10 and 50 nucleotides in length. It is most preferred that the oligonucleotide be between 15 and 25 nucleotides in length.

The nucleotides of the oligonucleotides may be any known in the art including natural and synthetic moieties. The term "oligonucleotide" as used herein refers to a polynucleotide formed from joined nucleotides. Moreover, the term "oligonucleotide" includes naturally occurring oligonucleotides or synthetic oligonucleotides formed from naturally occurring subunits or analogous subunits designed to confer special properties on the oligonucleotide so that it is more stable in biological systems or binds more tightly to target sequences. It also includes modifications of the oligonucleotides such as chemically linking them to other compounds that will enhance delivery to cells or to the nucleus and other compartments of cells. Oligonucleotides of the invention may be synthesized by any method known in the art, including synthetic chemical methods. See, e.g., Vu and Hirschbein, *Tetrahedron Lett.* 1991, 32:30005-30008. Oligonucleotides may be modified via chemical methods known to those skilled in the art, including encapsulation in liposomes, or chemical linkage to steroids, antibodies, and cell receptors.

A preferred embodiment of the invention is an oligonucleotide complementary to an endogenous MARCKS nucleotide sequence found in the cell to be treated, or having sufficient complementarity to allow stable interstrand hybridization between the oligonucleotide and an endogenous MARCKS nucleotide, and that inhibits the expression of the MARCKS gene. A preferred oligonucleotide is one that is complementary to a MARCKS nucleotide sequence derived or selected from a mammal, in particular, a human.

The oligonucleotides of the present invention may be oligodeoxyribonucleotides or oligoribonucleotides, including modified oligodeoxynucleotides and oligoribonucleotides. Moreover, the oligonucleotides of the invention may be comprised of combinations of deoxyribonucleotides and ribonucleotides. Further, oligonucleotides of the invention may also include modified subunits. For example, the invention may include phosphorothioate oligodeoxyribonucleotides. It is preferred that the oligonucleotides of the invention be modified to increase stability and prevent intracellular and extracellular degradation. It is more preferred that the oligonucleotides of the invention be modified to increase their affinity for target sequences, and their transport to the appropriate cells and cell compartments when they are delivered into a mammal in a pharmaceutically active form.

It is preferred that the oligonucleotides of the invention be antisense oligonucleotides. The oligonucleotides of the invention may be targeted to a non-coding portion of a MARCKS or targeted to coding sequences of the gene, and may include an intron-exon junction (i.e., several nucleotides on either or both sides of the intron-exon junction).

The oligonucleotides of the invention may be administered by any method that produces contact of the oligonucleotide with the target tissue or cell in the subject being treated, including but not limited to oral administration, topical administration, and inhalation. The pharmaceutical compositions comprising the oligonucleotides may be in solid dosage forms, such as capsules, tablets, and powders, or in liquid dosage forms, such as elixirs, syrups, and suspensions. The dosage administered varies depending upon factors such as: pharmacodynamic characteristics; its mode and route of administration; age, health, and weight of the recipient; nature and extent of symptoms; kind of concurrent treatment; and frequency of treatment and the effect desired. Effective dosages are those which are able to inhibit mucus production in the airways at a level which alleviates, reduces, or eliminates the symptoms or conditions associated with the mucus production.

The oligonucleotides may be administered singly, or in combination with other compounds of the invention, other pharmaceutical compounds, or therapies. The oligonucleotides are preferably administered with a pharmaceutical acceptable carrier or diluent selected on the basis of the selected route of administration and standard pharmaceutical practice.

Inhibition of secretion of mucus, via inhibition of MARCKS protein function in epithelial secretory cells, is a focus of this invention. To achieve this end, the invention provides methods of inhibiting mucus secretion which comprises contacting a mucus-secretory cell with a MARCKS gene expression inhibitory amount of an oligonucleotide substantially complementary to an endogenous MARCKS gene nucleotide sequence. The invention also includes a method whereby the contacting step comprises lipofectin as a carrier for the oligonucleotide. The oligonucleotides of the invention are administered to mammals or avians, and preferably to humans, in therapeutically effective amounts or concentrations which are effective to inhibit or reduce mucus production in the target tissue or organ.

The oligonucleotides of the invention will be capable of reaching their intracellular target to inhibit or reduce the expression of MARCKS protein therein. The invention therefore provides methods of inhibiting mucus secretion which comprise contacting at least one element of MARCKS gene expression machinery with a gene expression inhibitory amount of an oligonucleotide. For the purposes of the invention, the elements of the gene expression machinery may comprise any nucleotide sequence of a MARCKS gene, the nucleotide sequence of spliced mRNAs transcribed from a gene, unspliced RNAs and partially spliced RNAs transcribed from a gene, DNA-RNA hybrids comprising sequence derived from a gene, such as in actively transcribing genes, RNA transcribed from a gene bound to protein, and any molecule or structure known in the art to be involved in gene expression.

U.S. Pat. No. 5,858,784 to Debs et al. provides a method of administering nucleic acids to the lung cells of a subject by preparing a liposome-nucleic acid mixture suitable for nebulization, nebulizing the mixture, and depositing the resulting nebulized mixture in the lungs of the subject. The nucleic acid sequence may include DNA sequences which encode polypeptides which are directly or indirectly responsible for a therapeutic effect, or active nucleotide sequences such as antisense sequences and ribozymes. The nucleic acid constructs can be provided to the cells of the subject as expression cassettes; preferably, the construct does not become integrated into the host cell genome and is introduced into the host as part of a non-integrating expression vector. (The disclosures of all US patents cited herein are intended to be incorporated herein in their entirety.)

Double Stranded RNA and Ribozymes

It has recently been shown that the introduction of exogenous double-stranded RNA (dsRNA) can specifically disrupt the activity of genes containing homologous sequences, possibly by post-transcriptional effects. Montgomery et al., *Proc. Natl. Acad. Sci. USA* 95:15502 (1998); Ngo et al., *Proc. Natl. Acad. Sci. USA* 95:14687 (1998). Accordingly, the methods of the present invention may be carried out by introducing exogenous dsRNA into a mucus-secreting cell, where the dsRNA has sufficient sequence similarity to the RNA of an endogenous MARCKS gene to result in a reduction in MARCKS protein in the cell (compared to that which would occur in the absence of the exogenous dsRNA).

The administration of dsRNA may be carried out using the methods discussed above regarding peptide and antisense oligonucleotide administration.

In an alternate embodiment of the present invention, DNA encoding an enzymatic RNA molecule (ribozyme) may be introduced into the target cell. Ribozymes are directed against and cleave the mRNA transcript of the cell's endogenous MARCKS protein. DNA encoding enzymatic RNA molecules may be produced in accordance with known techniques (see e.g., U.S. Pat. No. 4,987,071. Production of such an enzymatic RNA molecule and disruption of MARCKS protein production affects mucus production by the target cell in essentially the same manner as production of an antisense RNA molecule.

Methods of Screening

The present invention also provides a method of screening compounds for their ability to affect (enhance or inhibit) mucus production. Combinatorial chemistry processes as are known in the art may be used to generate large numbers of structurally diverse compounds, which can then be screened. Such screening methods comprise providing a culture of mucus-secreting cells, such as the cultures of normal human bronchial epithelial cells described in Example 1 herein. A test compound is administered to the cells, and the cells may also be exposed to a compound known to stimulate mucus production (e.g., PMA, UTP, 8-bromo-cGMP). The test compound and the stimulatory compound may be administered to the cells, for example, by exposing the cells to media containing the compounds. The cells may, for example, be pre-incubated with the test compound first, then co-incubated with the stimulatory compound and the test compound. Alternatively, the pre-incubation step may be omitted. The ability of the test compound to bind to either the mucin granule membrane (or a mucin granule membrane-related receptor) or to endogenous MARCKS protein at the mucin granule membrane binding site is assessed by detecting whether the test compound inhibits binding of endogenous MARCKS to the mucin granule. Such detection can be carried out using methods known in the art, for example, by labelling the test compound with a detectable molecule.

Molecules detectable by spectroscopic, photochemical, biochemical, immunochemical, electrical and optical means are known. Optically detectable molecules include fluorescent labels (fluorescein, Texas Red, Green Fluorescent Protein). Methods for viewing intact cells are known, including real-time confocal laser-scanning microscopy and two-photon laser-scanning microscopy.

Mucus secreted by the cells may also be measured after a pre-determined time period, for example using an ELISA assay as is known in the art. The mucus secretion of the cells exposed to the test compound can also be compared to that of control cells that were not exposed to the test compound. A decrease in mucus secretion by the test cells compared to the control cells indicates that the test compound inhibits mucus secretion, and an increase in mucus secretion by the test cells compared to the control cells indicates that the test compound enhances mucus secretion.

The following examples are provided to more fully illustrate the present invention and should not be construed as limiting thereof.

EXAMPLE 1

In Vitro Assessment of Mucus Secretion

Cell Culture System: Expansion and cryopreservation. Primary normal human bronchial epithelial (NHBE) cells (Clonetics, San Diego, Calif.) were seeded into vented T75 tissue culture flasks (500 cells/cm$^2$) in bronchial epithelial basal medium (BEBM; Clonetics, San Diego, Calif.) containing 25 ng/ml human recombinant epidermal growth factor (EGF; Intergen, Purchase, N.Y.), 65 ng/ml bovine pituitary extract (prepared by the methods of Bertolero et al. *Exp Cell Res* 155:64, 1984), $5 \times 10^{-8}$M all-trans retinoic acid, 1.5 µg/ml bovine serum albumin (Intergen, Purchase, N.Y.), 20 IU/ml nystatin (Gibco, Grand Island, N.Y.), 0.5 µg/ml hydrocortisone, 5 µg/ml insulin, 10 µg/ml transferrin, 0.5 µg/ml epinephrine, 6.5 ng/ml triiodothyronine, 50 µg/ml gentamicin, and 50 µg/ml amphotericin-B (Clonetics; San Diego, Calif.). Once confluent, cultures were dissociated with trypsin/EDTA and frozen as passage-2 according to the methods of Clonetics Corporation.

Air-liquid interface culture of NHBE cells. Following the expansion, NHBE cells were cultured in air/liquid interface according to the methods of Gray and co-workers with minor modifications (Gray et al. *Am J Respir Cell Mol Biol* 14:104, 1996). The air-liquid interface culture was initiated by seeding NHBE cells (passage-2, $2 \times 10^4$ cells/cm$^2$) on Transwell-clear culture inserts (24.5 mm, 0.45 µm pore size; Costar, Cambridge, Mass.) that were thin coated with rat tail collagen, type I (Collaborative Research, Bedford, Mass.). Cells were cultured submerged to 70% confluency (5-7 days) in a 1:1 mixture of bronchial epithelial cell growth medium (Clonetics, San Diego, Calif.):Dulbecco's modified Eagles medium with high glucose (BEGM:DMEM-H), containing the same supplements as described above with the exception of EGF (0.5 ng/ml). When cultures were 70% confluent, the air-liquid interface was created by removing the apical medium, and the basal medium (BEGM:DMEM-H) was changed daily thereafter. Cells were then cultured for an additional 14 days in air-liquid interface, a total of 21 days in culture.

Mucus ELISA: Mucus secreted from the airway epithelial cells in vitro after stimulation by activators was assessed using an ELISA (antibody capture method) (E. Harlow, D. Lane. "Antibodies: A Laboratory Manual." New York: Cold Spring Harbor Laboratory Press, 1988), wherein the collected mucus is bound directly to the ELISA plate. Mucus was detected using an antibody raised against monkey airway mucus (Lin et al. *Am J Respir Cell Mol Biol* 1:41, 1989).

EXAMPLE 2

MARCKS mRNA in Human Bronchial Epithelial Cells

MARCKS messenger RNA was detected in human bronchial epithelial cells grown in air/liquid interface culture by Northern analysis (Ausubel et al., eds. "Current Protocols in Molecular Biology." New York: John Wiley & Sons, 1992) using a human MARCKS cDNA (approximate length 1 kb) as a radiolabelled probe. MARCKS message increases as these cells become more differentiated when maintained in an air/liquid interface culture.

To detect MARCKS protein in these cells, cells were labeled with $^3$H-myristic acid (as MARCKS is myristoylated) for 16 hours in media. Cells were lysed, and MARCKS protein was immunoprecipitated according to the method of Spizz & Blackshear (*J Biol Chem* 271:553, 1996) using monoclonal antibody 2F12 (a gift from the Blackshear laboratory).

MARCKS within the airway epithelial cells was found to be phosphorylated by the PKC activator, PMA (100 nM), while 4α-PMA (a phorbol ester control which does not activate PKC), did not phosphorylate MARCKS. Phosphorylation of MARCKS by PMA was attenuated by Calphostin C (500 nM). NHBE cells also contained substantial amounts of cGMP-dependent protein kinase type 1α (PKG-1α) activity, which was localized to the cytosolic fraction. The cells exhibited constitutive PKG activity which was increased by incubation with 100 μM dibutyryl cGMP. In addition, the phosphorylation of MARCKS induced by PMA was reversed by incubation with 8-Br-cGMP (10 μM). Okadaic acid (500 nM) inhibited this effect. These results indicate that 8-Br-cGMP activates a phosphatase (type 1 or 2A), which dephosphorylates MARCKS.

EXAMPLE 3

Blocking of Mucin Secretion by Peptide MANS

The effect on mucus secretion of a myristoylated peptide containing the first 24 amino acids of the human MARCKS protein (MANS; myristoylated N-terminal sequence; SEQ ID NO:1) was tested. Cultured normal human bronchial epithelial cells as described above were used. Test cells were co-incubated for 15 minutes in apical and basolateral media containing 1, 10 or 100 μM of MANS peptide, and then co-incubated for 15 minutes with the peptide and 100 nM PMA plus 1 μM 8-Br-cGMP (columns 3-5 of FIG. 1A). Control cells were not exposed to MANS peptide but were preincubated in media only (column 1 of FIG. 1A) or media containing PMA and 8-Br-cGMP (column 2 of FIG. 1A). Single asterisks (*) indicate that the response was statistically different than the media control (column 1), and double asterisks (**) indicate that the response was statistically different than that observed in stimulated cells that were not exposed to the MANS peptide (column 2).

Stimulation by PMA and 8-Br-cGMP caused at least a 100% increase in mucus secretion over control levels. This increase, however, was blocked by pre- and co-incubation with the MANS peptide. Levels of secreted mucus fell to control values when 10 μM peptide was used, and levels of secreted mucus were well below control values following incubation with 100 μM MANS peptide (FIG. 1A).

The MANS peptide (100 μM) was also found to decrease constitutive (basal) mucus secretion by one hour incubation. Cells were treated as described above except that no PMA or 8-Br-cGMP was used. In addition, a negative control peptide of the same amino acid composition as the MANS peptide in random order (RNS; random N-terminal sequence) did not affect constitutive mucus secretion. Results are graphed in FIG. 1B. Single asterisk (*) indicates that the response was statistically different than the media control (column 1).

EXAMPLE 4

UTP-Induced Mucin Secretion is Blocked by Peptide Mans

These experiments were carried out similarly to those described in Example 3. To test for stimulated secretion, the cells were exposed apically and basolaterally to uridine 5'-triphosphate (UTP) at a concentration of 0.1 mM in media. Cells were pre-incubated for 15 minutes with the MANS peptide and test cultures were then co-incubated with the MANS peptide and UTP for 45 minutes.

Results are shown in FIG. 2, where column 1 is the media/control; column 2=0.1 mM UTP; column 3=0.1 mM UTP and 1 μM MANS peptide; column 4=0.1 mM UTP and 10 μM MANS peptide; and column 5=0.1 mM UTP and 100 μM MANS peptide. Single asterisks (*) indicate that the measured response was statistically different than the media control (column 1), and double asterisks (**) indicate that the response was statistically different than that observed in stimulated cells that were not exposed to the MANS peptide (column 2). The MANS peptide at 10 and 100 μM significantly reduced UTP-stimulated mucus secretion.

EXAMPLE 5

Effect of MA-PSD Peptide on Mucin Secretion

These experiments were carried out using normal human bronchial epithelial cells in vitro as described above. A myristoylated peptide composed of the 25 amino acid phosphorylation site domain of MARCKS (MA-PSD peptide; SEQ ID NO:2) was prepared. Test cells were preincubated for 15 minutes in apical and basolateral media containing the MA-PSD peptide (1, 10 or 100 μM), and then co-incubated for 15 minutes with the peptide and stimulus (100 nM PMA plus 1 μM 8-Br-cGMP). Control cells were preincubated in media only (column 1 of FIG. 3A); or with 100 nM PMA only (column 2); or with 100 nM PMA and 1 μM 8-Br-cGMP (column 3)

Stimulation by PMA and 8-Br-cGMP caused about a 100% increase in mucus secretion over control levels. This increase was augmented in a dose-dependent manner by pre- and co-incubation with the MA-PSD peptide, 1 or 10 μM. Interestingly, stimulated levels of mucus secretion were unaffected by the presence of 100 μM peptide. Results are graphed in FIG. 3A. Results using MANS peptide (1, 10 and 100 μM) are provided in columns 7-9 for comparison. Single asterisks (*) indicate that the measured response was statistically different than the media control (column 1), and double asterisks (**) indicate that the response was statistically different than that observed in stimulated cells that were not exposed to the peptide (column 3).

The effect of MA-PSD peptide (1, 10 and 100 μM) on basal mucin secretion was also measured. Cells as described above were incubated for one hour with the MA-PSD peptide (no PMA or 8-Br-cGMP). Results are graphed in FIG. 3B. The single asterisk (*) indicates that the response to 100 μM of MA-PSD peptide was statistically different than the media control (column 1), whereas no statistically significant difference was seen when 1 or 10 μM of peptide was used (columns 3 and 4).

EXAMPLE 6

Inhibition of Mucus Secretion by Antisense Oligonucleotides

Using an antisense oligonucleotide directed to the endogenous human MARCKS gene, mucus secretion was inhibited in vitro in human airway epithelial cells. The in vitro assay system as described in Example 1 was utilized to test the effects of antisense oligonucleotides to MARCKS mRNA.

An antisense oligonucleotide was constructed by a commercial supplier (Chemicon International, Temecula, Calif.; in conjunction with Biognostik GmbH, Gottingen, Germany) based on the human MARCKS gene sequence of Sakai et al. (*Genomics* 14:175 (1992); GenBank accession number D10522, D90498). A control oligonucleotide was also constructed.

The oligonucleotides were administered to the differentiated airway epithelial cultures by incubation in media containing the oligonucleotides (5 μM) for three days. The oligonucleotide was supplied to the apical surface of the cells in 0.4 ml of media containing lipofectin reagent (2 μg/ml; Gibco BRL). Cells were incubated with the oligonucleotide in the presence of lipofectin for 24 hours. Following a media change, cells were incubated with the oligonucleotide alone for an additional 48 hours. To test the ability of the oligonucleotides to affect stimulated mucus secretion, test cells were stimulated for 15 minutes with 100 nM PMA and 1 μM 8-Br-cGMP (activators of PKC and PKG, respectively).

Figure 5:
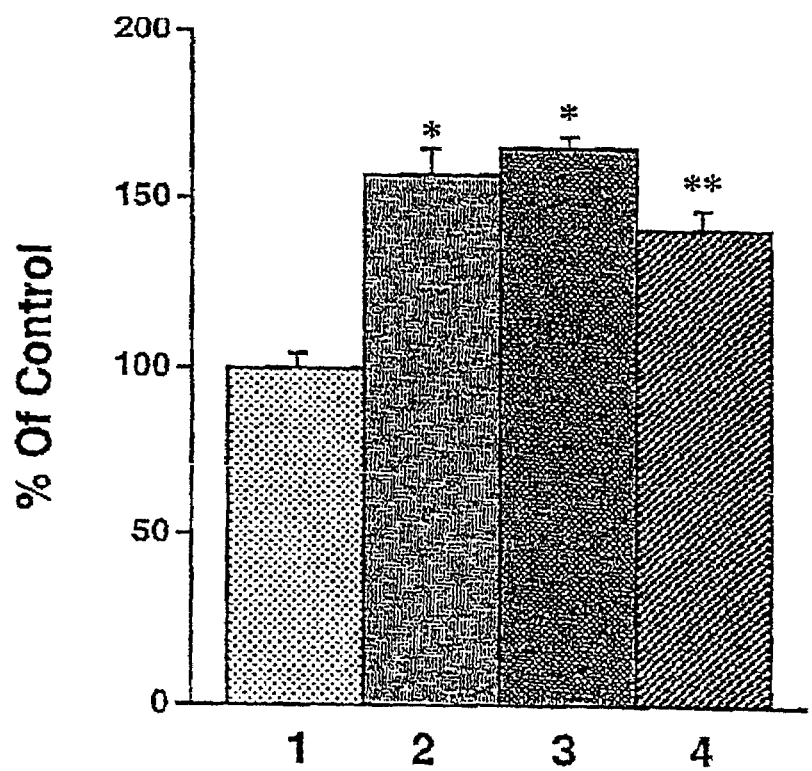
FIG. 5 is a graph of the effects of a MARCKS antisense oligonucleotide on stimulated mucin secretion by human bronchial epithelial cells in vitro. Column 1=media/control; column 2=cells stimulated with 100 nM PMA and 1 µM 8-Br-cGMP; column 3=5 µM control oligonucleotide, 100 nM PMA and 1 µM 8-Br-cGMP; column 4=5 µM antisense oligonucleotide, 100 nM PMA and 1 µM 8-Br-cGMP. Single asterisks (*) indicate that the measured response was statistically different than the media control (column 1), and double asterisks (**) indicate that the response was statistically different than that observed in stimulated cells that were not exposed to the any oligonucleotide (column 2).

Results are shown in FIG. 5, where column 1=media/control; column 2=cells stimulated with PMA and 8-Br-cGMP; column 3=cells exposed to 5 μM control oligonucleotide and stimulated with PMA and 8-Br-cGMP; and column 4=cells exposed to 5 μM antisense oligonucleotide and stimulated with PMA and 8-Br-cGMP. Single asterisks (*) indicate that the measured response was statistically different than the media control (column 1), and double asterisks (**) indicate that the response was statistically different than that observed in stimulated cells that were not exposed to an oligonucleotide (column 2).

Mucus secreted from the airway epithelial cells after stimulation by PKC and PKG activators was assessed using an ELISA (antibody capture method). The control oligonucleotide (column 3) had no effect on stimulated mucus secretion. In contrast, the antisense oligonucleotide (column 4) caused a statistically significant decrease in mucus secretion compared to stimulated levels.

These results indicate that MARCKS antisense oligonucleotides inhibit stimulated mucus secretion, although a basal level of mucus secretion can be maintained by selection of appropriate dosages. In contrast, control oligonucleotides had no effect on stimulated secretion.

EXAMPLE 7

TNF-α Up-Regulates MARCKS Expression and Augments Mucin Hypersecretion

NHBE cells were incubated with 10 ng/ml human recombinant TNF-α or medium alone for 4 hrs, then stimulated with PMA (100 nM)+8-Br-cGMP (1 μM) for 15 min, or UTP (0.1 mM) for 2 hrs. Secreted mucin was collected and measured by ELISA. Total RNA and protein were isolated from treated cells. MARCKS mRNA was assessed by Northern hybridization, and protein by Western blotting. The results are shown in FIGS. 6A, 6B and 6C.

Figure 6:
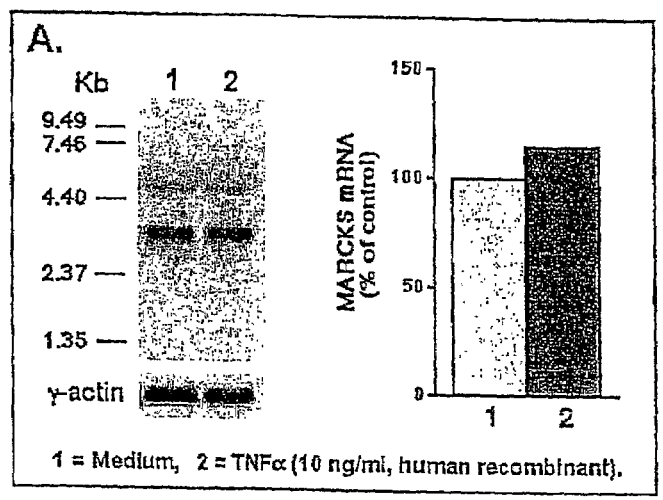
FIGS. 6A, 6B, and 6C together illustrate that TNF-α up-regulates MARCKS expression and augments mucin hypersecretion. NHBE cells were incubated with 10 ng/ml human recombinant TNF-α or medium alone for 4 hrs, then stimulated with PMA (100 nM)+8-Br-cGMP (1 µM) for 15 min, or UTP (0.1 mM) for 2 hrs. Secreted mucin was collected and measured by ELISA. Total RNA and protein were isolated from treated cells. MARCKS mRNA was assessed by Northern hybridization, and MARCKS protein by the Western Blot technique.
Figure 6:
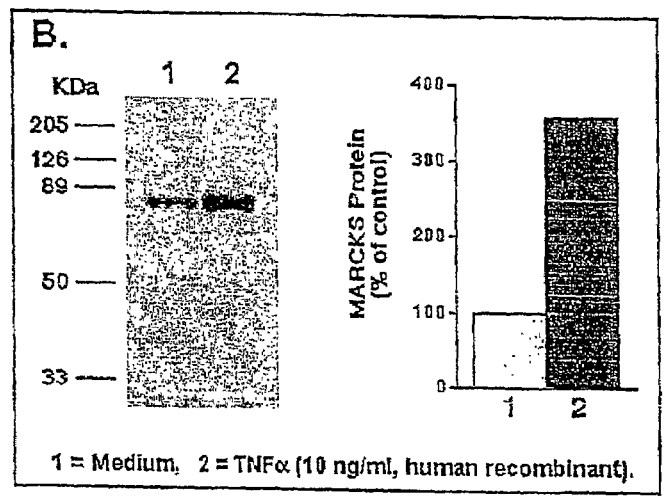
Figure 6:
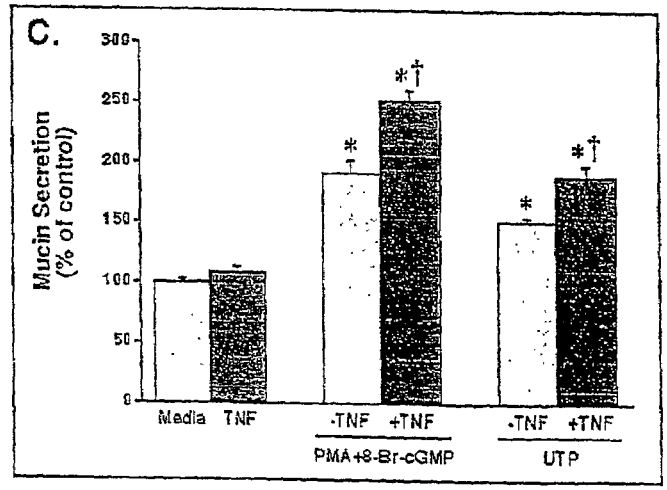

The Northern Blot and graph shown in FIG. 6A show an increase in MARCKS mRNA in cells incubated with TNF-α (lane 2 of blot, column 2 of graph) compared to cells incubated in medium alone (lane 1 of blot, column 1 of graph). The Western-blot and graph shown in FIG. 6B show a three- to four-fold increase in MARCKS protein in cells incubated with TNF-α (lane 2 of blot, column 2 of graph) as compared with cells incubated with medium only (lane 1 of blot, column 1 of graph). The graph in FIG. 6C shows that in cells incubated with TNF-α, mucin hypersecretion was significantly augmented in response to subsequent stimulation by PMA+8-Br-cGMP or UTP when compared to mucin secretion of cells incubated in medium only. Data are presented as mean±SEM (n=6 at each point). Single asterisks (*) indicate a statistically significant difference from control (medium-only) samples (p<0.05). Single cross marks (†) indicate a statistically significant difference from stimulus (p<0.05).

EXAMPLE 8

Okadaic Acid Blocks Stimulated Mucin Hypersecretion

NHBE cells were pre-incubated with okadaic acid (500 nM) for 15 min at 37° C./5% $CO_2$, then stimulated with PMA (100 nM)+8-Br-cGMP (1 μM) for 15 min, or with UTP (0.1 mM) for 2 hours. Secreted mucin in the apical medium was collected and assayed by ELISA. The results are shown in FIG. 7.

Figure 7:
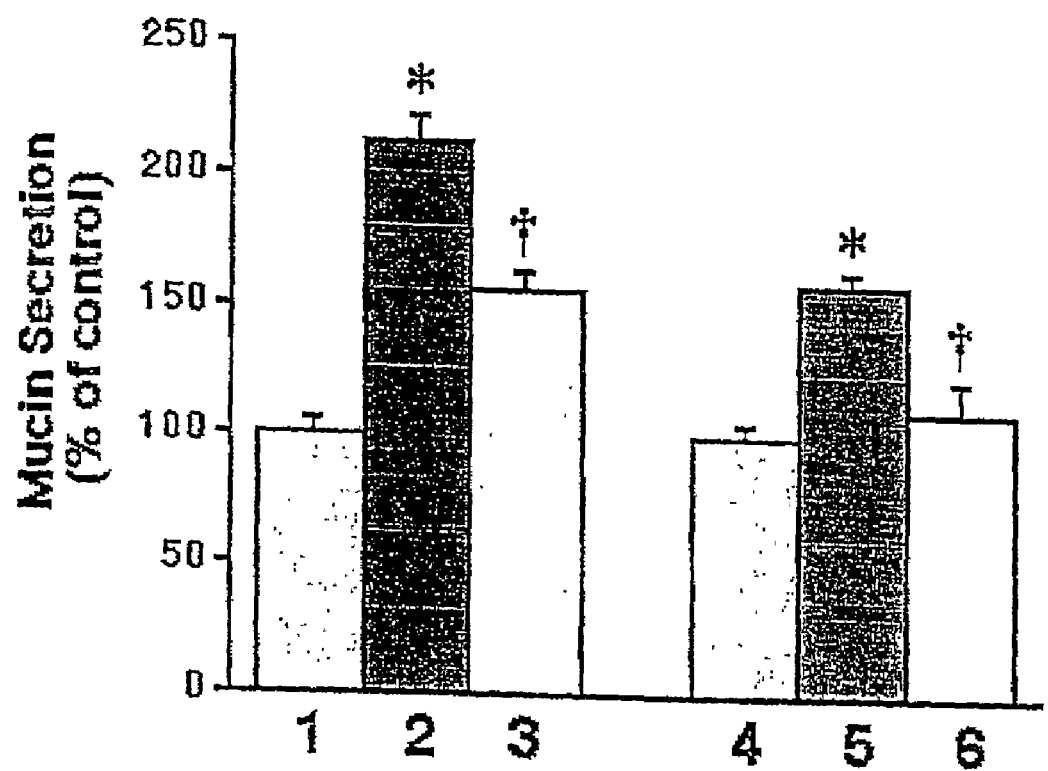
FIG. 7 is a graph showing that okadaic acid, a phosphatase inhibitor, blocks mucin hypersecretion induced by PMA+8-Br-cGMP or UTP. NHBE cells were pre-incubated with okadaic acid (500 nM) for 15 min at 37° C./5% $CO_2$, then stimulated with PMA (100 nM)+8-Br-cGMP (1 µM) for 15 min, or with UTP (0.1 mM) for 2 hours. Secreted mucin in the apical medium was collected and assayed by ELISA. Column 1 shows the results of incubation with medium alone for 30 min. Column 2 shows the results of pre-incubation with medium alone for 15 min, then incubation with PMA+8-Br-cGMP for an additional 15 min. Column 3 shows the results of pre-incubation with okadaic acid for 15 min, then co-incubation with PMA+8-Br-cGMP for an additional 15 min. Column 4 shows the results of incubation with medium alone for 2 hrs. Column 5 shows the results of pre-incubation with medium alone for 15 min, then incubation with UTP for an additional 2 hrs. Column 6 shows the results of pre-incubation with okadaic acid for 15 min, then co-incubation with UTP for an additional 2 hrs. Data are presented as mean±SEM (n=6 at each point). Single asterisks (*) indicate a statistically significant difference from control p<0.05). Single cross marks (†) indicate statistically significant difference from stimulus (p<0.05).

The graph shown in FIG. 7 shows that okadaic acid, a phosphatase inhibitor, blocks mucin hypersecretion induced by PMA+8-Br-cGMP or UTP. Column 1 shows the results of incubation with medium alone for 30 min. Column 2 shows the results of pre-incubation with medium alone for 15 min, then incubation with PMA+8-Br-cGMP for an additional 15 min. Column 3 shows the results of pre-incubation with okadaic acid for 15 min, then co-incubation with PMA+8-Br-cGMP for an additional 15 min. Column 4 shows the results of incubation with medium alone for 2 hrs. Column 5 shows the results of pre-incubation with medium alone for 15 min, then incubation with UTP for an additional 2 hrs. Column 6 shows the results of pre-incubation with okadaic acid for 15 min, then co-incubation with UTP for an additional 2 hrs. Data are presented as mean±SEM (n=6 at each point). Single asterisks (*) indicate a statistically significant difference from control (p<0.05). Single cross marks (†) indicate statistically significant difference from stimulus (p<0.05).

EXAMPLE 9

Mucin Hypersecretion Induced by UTP is Inhibited by Inhibitors of the Mucus Secretion Signaling Pathway NHBE cells were pre-incubated with the indicated inhibitor for 15 min, then stimulated with UTP (0.1 mM) for 2 hours. Secreted mucin in the apical medium was collected and assayed by ELISA. The results are shown in FIG. 8.

Figure 8:
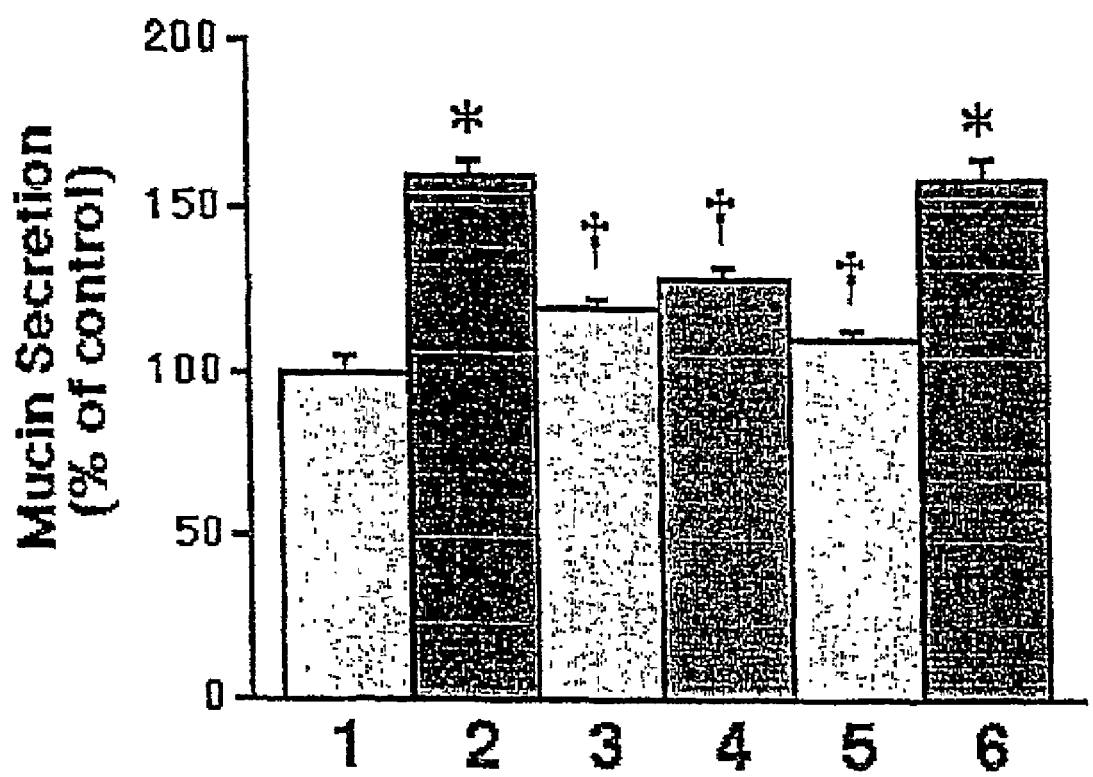
FIG. 8 is a graph showing that mucin hypersecretion induced by UTP involves activation of PKC and PKG. NHBE cells were pre-incubated with the indicated inhibitor (described below) for 15 min, then stimulated with UTP (0.1 mM) for 2 hours. Secreted mucin in the apical medium was collected and assayed by ELISA. Column 1 indicates the results of incubation with medium alone. Column 2 indicates the results of incubation with 0.1 mM UTP. Column 3 indicates the results of incubation with 0.1 mM UTP+500 nM calphostin C (an inhibitor of PKC). Column 4 indicates the results of incubation with 0.1 mM UTP+10 µM Rp-8-Br-PET-cGMP (an inhibitor of PKG). Column 5 indicates the results of incubation with 0.1 mM UTP+50 µM LY83583 (an inhibitor of soluble guanylyl cyclase). Column 6 indicates the results of incubation with 0.1 mM UTP+500 nM KT5720 (an inhibitor of PKA). Data are presented as mean±SEM (n=6 at each point). Single asterisks (*) indicate a statistically significant difference from control p<0.05). Single cross marks (†) indicate a statistically significant difference from UTP stimulation (p<0.05).

The graph of FIG. 8 shows that mucin hypersecretion induced by UTP involves activation of PKC and PKG. Column 1 indicates the results of incubation with medium alone. Column 2 indicates the results of incubation in 0.1 mM UTP. Column 3 indicates the results of incubation in 0.1 mM UTP+500 nM calphostin C (an inhibitor of PKC). Column 4 indicates the results of incubation with 0.1 mM UTP+10 μM Rp-8-Br-PET-cGMP (an inhibitor of PKG). Column 5 indicates the results of incubation with 0.1 mM UTP+50 μM LY83583 (an inhibitor of soluble guanylyl cyclase). Column 6 indicates the results of incubation with 0.1 mM UTP+500 nM KT5720 (an inhibitor of PKA). Data are presented as mean±SEM (n=6 at each point). Single asterisks (*) indicate a statistically significant difference from control (p<0.05). Single cross marks (†) indicate a statistically significant difference from UTP stimulation (p<0.05).

The foregoing is illustrative of the present invention, and is not to be construed as limiting thereof. The invention is defined by the following claims, with equivalents of the claims to be included therein.

We claim:

1. A method of reducing mucus hypersecretion in the airways of a subject suffering from asthma comprising administration to the airways of said subject a pharmaceutical formulation comprising a mucus-inhibitory amount of a N-terminal myristoylated peptide selected from the group consisting of the MANS peptide and a N-terminal myristoylated peptide fragment thereof comprising at least the first 10 amino acids of the MANS peptide, wherein said MANS peptide consists of a N-terminal myristoylated peptide of SEQ ID NO: 1, wherein said N-terminal myristoylated peptide reduces MARCKS protein-related mucus hypersecretion, and whereby mucus hypersecretion in said airways is reduced compared to that which would occur in the absence of said peptide.

2. The method according to claim 1, further comprising removal of retained mucus secretions from the airways of said mammalian subject prior to administration of said formulation.

3. The method according to claim 1, wherein said administration is by inhalation.

4. A pharmaceutical formulation comprising a N-terminal myristoylated peptide selected from the group consisting of the MANS peptide and a N-terminal myristoylated peptide fragment thereof comprising at least the first 10 amino acids of the MANS peptide, wherein said MANS peptide consists of a N-terminal myristoylated peptide of SEQ ID NO:1, wherein said N-terminal myristoylated peptide reduces MARCKS protein-related mucus hypersecretion, and a pharmaceutically acceptable carrier.

5. The pharmaceutical formulation according to claim 4, wherein said formulation is aerosolized.

6. The pharmaceutical formulation according to claim 4, wherein said peptide is contained within liposomes.

7. The method according to claim 1, wherein said N-terminal myristoylated peptide fragment comprises at least the first 15 contiguous amino acids of the MANS peptide.

8. The pharmaceutical formulation according to claim 4, wherein said N-terminal myristoylated peptide fragment comprises at least the first 15 contiguous amino acids of the MANS peptide.

9. The method according to claim 1, wherein said N-terminal myristoylated peptide fragment comprises at least the first 20 contiguous amino acids of the MANS peptide.

10. The pharmaceutical formulation according to claim 4, wherein said N-terminal myristoylated peptide consists of fragment comprises at least the first 20 contiguous amino acids of the MANS peptide.

* * * * *

UNITED STATES PATENT AND TRADEMARK OFFICE
CERTIFICATE OF CORRECTION

PATENT NO. : 7,265,088 B1  Page 1 of 1
APPLICATION NO. : 09/914020
DATED : September 4, 2007
INVENTOR(S) : Li et al.

It is certified that error appears in the above-identified patent and that said Letters Patent is hereby corrected as shown below:

Column 3, Line 67: Please correct "M-PSD"
　　　　　　　　　　To read -- MA-PSD--

Column 5, Line 34: Please correct: "control p<0.05)."
　　　　　　　　　　To read -- control (p<0.05).--

Column 5, Line 53: Please correct: "control p<0.05)."
　　　　　　　　　　To read -- control (p<0.05).--

Column 40, Claim 10 Line 5, Please correct to read:
　　　　--10. The pharmaceutical formulation according to claim 4, wherein said N-terminal myristoylated peptide fragment comprises at least the first 20 contiguous amino acids of the MANS peptide.--

Signed and Sealed this

Fourth Day of December, 2007

JON W. DUDAS
*Director of the United States Patent and Trademark Office*

SEQUENCE LISTING

<160> NUMBER OF SEQ ID NOS: 6

<210> SEQ ID NO 1
<211> LENGTH: 24
<212> TYPE: PRT
<213> ORGANISM: Homo Sapiens

<400> SEQUENCE: 1

Gly Ala Gln Phe Ser Lys Thr Ala Ala Lys Gly Glu Ala Ala Glu
1               5                   10                  15

Arg Pro Gly Glu Ala Ala Val Ala
            20

<210> SEQ ID NO 2
<211> LENGTH: 25
<212> TYPE: PRT
<213> ORGANISM: Homo Sapiens

<400> SEQUENCE: 2

Lys Lys Lys Lys Lys Arg Phe Ser Phe Lys Lys Ser Phe Lys Leu Ser
1               5                   10                  15

Gly Phe Ser Phe Lys Lys Asn Lys Lys
            20                  25

<210> SEQ ID NO 3
<211> LENGTH: 1885
<212> TYPE: DNA
<213> ORGANISM: Homo Sapiens
<220> FEATURE:
<221> NAME/KEY: CDS
<222> LOCATION: (309)..(1307)
<223> OTHER INFORMATION:

<400> SEQUENCE: 3

```
tttattactt cttttttttt cgaactacac ttgggctcct ttttttgtgc tcgactttc      60 caccctttt ccctccctcc tgtgctgctg cttttgatc tcttcgacta aaatttttt      120 atccggagtg tatttaatcg gttctgttct gtcctctcca ccaccccac cccctcct       180 ccggtgtgtg tgccgctgcc gctgttgccg ccgccgctgc tgctgctgct cgccccgtcg   240
ttacaccaac ccgaggctct tgtttcccc tcttggatct gttgagtttc tttgttgaag    300 aagccagc atg ggt gcc cag ttc tcc aag acc gca gcg aag gga gaa gcc       350
         Met Gly Ala Gln Phe Ser Lys Thr Ala Ala Lys Gly Glu Ala
             1               5                   10 gcc gcg gag agg cct ggg gag gcg gct gtg gcc tcg tcg cct tcc aaa       398
Ala Ala Glu Arg Pro Gly Glu Ala Ala Val Ala Ser Ser Pro Ser Lys
15                  20                  25                  30 gcg aac gga cag gag aat ggc cac gtg aag gta aac ggc gac gct tcg       446
Ala Asn Gly Gln Glu Asn Gly His Val Lys Val Asn Gly Asp Ala Ser
                35                  40                  45 ccc gcg gcc gcc gag tcg ggc gcc aag gag gag ctg cag gcc aac ggc       494
Pro Ala Ala Ala Glu Ser Gly Ala Lys Glu Glu Leu Gln Ala Asn Gly
    50                  55                  60 agc gcc ccg gcc gcc gac aag gag gag ccc gcg gcc gcc ggg agc ggg       542
Ser Ala Pro Ala Ala Asp Lys Glu Glu Pro Ala Ala Ala Gly Ser Gly
65                  70                  75 gcg gcg tcg ccc tcc gcg gcc gag aaa ggt gag ccg gcc gcc gcc gct       590
Ala Ala Ser Pro Ser Ala Ala Glu Lys Gly Glu Pro Ala Ala Ala Ala
80                  85                  90 gcc ccc gag gcc ggg gcc agc ccg gta gag aag gag gcc ccc gcg gaa       638
```

| | | |
|---|---|---|
| Ala Pro Glu Ala Gly Ala Ser Pro Val Glu Lys Glu Ala Pro Ala Glu<br>95                                      100                       105                    110 | | |
| ggc gag gct gcc gag ccc ggc tcg ccc acg gcc gcg gag gga gag gcc<br>Gly Glu Ala Ala Glu Pro Gly Ser Pro Thr Ala Ala Glu Gly Glu Ala<br>                         115                      120                     125 | 686 |
| gcg tcg gcc gcc tcc tcg act tct tcg ccc aag gcc gag gac ggg gcc<br>Ala Ser Ala Ala Ser Ser Thr Ser Ser Pro Lys Ala Glu Asp Gly Ala<br>             130                      135                   140 | 734 |
| acg ccc tcg ccc agc aac gag acc ccg aaa aaa aaa aag aag cgc ttt<br>Thr Pro Ser Pro Ser Asn Glu Thr Pro Lys Lys Lys Lys Lys Arg Phe<br>           145                      150                   155 | 782 |
| tcc ttc aag aag tct ttc aag ctg agc ggc ttc tcc ttc aag aag aac<br>Ser Phe Lys Lys Ser Phe Lys Leu Ser Gly Phe Ser Phe Lys Lys Asn<br>160                           165                     170 | 830 |
| aag aag gag gct gga gaa ggc ggt gag gct gag gcg ccc gct gcc gaa<br>Lys Lys Glu Ala Gly Glu Gly Gly Glu Ala Glu Ala Pro Ala Ala Glu<br>175                         180                   185               190 | 878 |
| ggc ggc aag gac gag gcc gcc ggg ggc gca gct gcg gcc gcc gcc gag<br>Gly Gly Lys Asp Glu Ala Ala Gly Gly Ala Ala Ala Ala Ala Ala Glu<br>                 195                     200                   205 | 926 |
| gcg ggc gcg gcc tcc ggg gag cag gca gcg gcg ccg ggc gag gag gca<br>Ala Gly Ala Ala Ser Gly Glu Gln Ala Ala Ala Pro Gly Glu Glu Ala<br>           210                      215                   220 | 974 |
| gca gcg ggc gag gag ggg gcg gcg ggt ggc gac tcg cag gag gcc aag<br>Ala Ala Gly Glu Glu Gly Ala Ala Gly Gly Asp Ser Gln Glu Ala Lys<br>               225                     230                   235 | 1022 |
| ccc cag gag gcc gct gtc gcg cca gag aag ccg ccc gcc agc gac gag<br>Pro Gln Glu Ala Ala Val Ala Pro Glu Lys Pro Pro Ala Ser Asp Glu<br>240                           245                   250 | 1070 |
| acc aag gcc gcc gag gag ccc agc aag gtg gag gag aaa aag gcc gag<br>Thr Lys Ala Ala Glu Glu Pro Ser Lys Val Glu Glu Lys Lys Ala Glu<br>255                           260                   265               270 | 1118 |
| gag gcc ggg gcc agc gcc gcc gcc tgc gag gcc ccc tcc gcc gcc ggg<br>Glu Ala Gly Ala Ser Ala Ala Ala Cys Glu Ala Pro Ser Ala Ala Gly<br>               275                     280                   285 | 1166 |
| ctg gtg tgc ccc cgg aga gga ggc agc ccc cgc gga gga gcc cgc ggc<br>Leu Val Cys Pro Arg Arg Gly Gly Ser Pro Arg Gly Gly Ala Arg Gly<br>           290                      295                   300 | 1214 |
| cgc cgc agc ctc aat caa gcc tgc gca gcc ccc tca cag gag gcc cag<br>Arg Arg Ser Leu Asn Gln Ala Cys Ala Ala Pro Ser Gln Glu Ala Gln<br>           305                      310                   315 | 1262 |
| ccc gag tgc agt cca gaa gcc ccc cca gcg gag gcg gca gag taa<br>Pro Glu Cys Ser Pro Glu Ala Pro Pro Ala Glu Ala Ala Glu<br>320                           325                   330 | 1307 |
| aagagcaagc ttttgtgaga taatcgaaga acatttctc ccccgtttgt ttggttggag | 1367 |
| tggtgccagg tactggattt tggagaactt gtctacaacc agggattgat tttaaagatg | 1427 |
| tcttttttta ttttactttt ttttaagcac caaattttgt tgtttttttt ttctcccctc | 1487 |
| cccacagatc ccatctcaaa tcattctgtt aaccaccatt ccaacaggtc gaggagagct | 1547 |
| taaacacctt cttcctctgg ccttgtttct cttttatttt ttattttttc gcatcagtat | 1607 |
| taatgttttt gcatactttg catctttatt caaaagtgta aactttcttt gtcaatctat | 1667 |
| ggacatgccc atatatgaag gagatgggtg ggtcaaaaag ggatatcaaa tgaagtgata | 1727 |
| ggggtcacaa tggggaaatt gaagtggtgc ataacattgc caaaatagtg tgccactaga | 1787 |
| aatggtgtaa aggctgtctt tttttttttt tttaagaaaa agttattacc atgtattttg | 1847 |
| tgaggcaggt ttacaacact acaactcgtg ccgaattc | 1885 |

```
<210> SEQ ID NO 4
<211> LENGTH: 332
<212> TYPE: PRT
<213> ORGANISM: Homo Sapiens

<400> SEQUENCE: 4

Met Gly Ala Gln Phe Ser Lys Thr Ala Ala Lys Gly Glu Ala Ala
1               5                   10                  15

Glu Arg Pro Gly Glu Ala Ala Val Ala Ser Ser Pro Ser Lys Ala Asn
                20                  25                  30

Gly Gln Glu Asn Gly His Val Lys Val Asn Gly Asp Ala Ser Pro Ala
            35                  40                  45

Ala Ala Glu Ser Gly Ala Lys Glu Glu Leu Gln Ala Asn Gly Ser Ala
        50                  55                  60

Pro Ala Ala Asp Lys Glu Glu Pro Ala Ala Gly Ser Gly Ala Ala
65                  70                  75                  80

Ser Pro Ser Ala Ala Glu Lys Gly Glu Pro Ala Ala Ala Ala Pro
                85                  90                  95

Glu Ala Gly Ala Ser Pro Val Glu Lys Glu Pro Ala Glu Gly Glu
                100                 105                 110

Ala Ala Glu Pro Gly Ser Pro Thr Ala Ala Glu Gly Glu Ala Ala Ser
        115                 120                 125

Ala Ala Ser Ser Thr Ser Ser Pro Lys Ala Glu Asp Gly Ala Thr Pro
    130                 135                 140

Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190

Lys Asp Glu Ala Ala Gly Gly Ala Ala Ala Ala Ala Glu Ala Gly
        195                 200                 205

Ala Ala Ser Gly Glu Gln Ala Ala Ala Pro Gly Glu Glu Ala Ala Ala
    210                 215                 220

Gly Glu Glu Gly Ala Ala Gly Gly Asp Ser Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
            260                 265                 270

Gly Ala Ser Ala Ala Ala Cys Glu Ala Pro Ser Ala Ala Gly Leu Val
        275                 280                 285

Cys Pro Arg Arg Gly Gly Ser Pro Arg Gly Gly Ala Arg Gly Arg Arg
    290                 295                 300

Ser Leu Asn Gln Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330

<210> SEQ ID NO 5
<211> LENGTH: 2589
<212> TYPE: DNA
<213> ORGANISM: Homo Sapiens
<220> FEATURE:
<221> NAME/KEY: CDS
<222> LOCATION: (370)..(1368)
```

<223> OTHER INFORMATION:

<400> SEQUENCE: 5

```
caaccaggga gatttctcca tttcctctct gtctacagtg cggctacaaa tctgggattt      60
ttttattact tcttttttt tcgaactaca cttgggctcc ttttttgtg ctcgactttt      120 ccacccttt tccctccctc ctgtgctgct gcttttgat ctcttcgact aaaattttt       180 tatccggagt gtatttaatc ggttctgttc tgtcctctcc accacccca ccccctccc      240 tccggtgtgt gtgccgctgc cgctgttgcc gccgccgctg ctgctgctgc tcgcccgtc     300 gttacaccaa cccgaggctc tttgtttccc ctcttggatc tgttgagttt ctttgttgaa    360 gaagccagc atg ggt gcc cag ttc tcc aag acc gca gcg aag gga gaa gcc    411
          Met Gly Ala Gln Phe Ser Lys Thr Ala Ala Lys Gly Glu Ala
           1               5                  10 gcc gcg gag agg cct ggg gag gcg gct gtg gcc tcg tcg cct tcc aaa      459
Ala Ala Glu Arg Pro Gly Glu Ala Ala Val Ala Ser Ser Pro Ser Lys
 15              20                  25                  30 gcg aac gga cag gag aat ggc cac gtg aag gta aac ggc gac gct tcg      507
Ala Asn Gly Gln Glu Asn Gly His Val Lys Val Asn Gly Asp Ala Ser
             35                  40                  45 ccc gcg gcc gcc gag tcg ggc gcc aag gag gag ctg cag gcc aac ggc      555
Pro Ala Ala Ala Glu Ser Gly Ala Lys Glu Glu Leu Gln Ala Asn Gly
         50                  55                  60 agc gcc ccg gcc gcc gac aag gag gag ccc gcg gcc gcc ggg agc ggg      603
Ser Ala Pro Ala Ala Asp Lys Glu Glu Pro Ala Ala Ala Gly Ser Gly
 65                  70                  75 gcg gcg tcg ccc tcc tcg gcc gag aaa ggt gag ccg gcc gcc gcc gct      651
Ala Ala Ser Pro Ser Ser Ala Glu Lys Gly Glu Pro Ala Ala Ala Ala
         80                  85                  90 gcc ccc gag gcc ggg gcc agc ccg gta gag aag gag gcc ccc gcg gaa      699
Ala Pro Glu Ala Gly Ala Ser Pro Val Glu Lys Glu Ala Pro Ala Glu
 95                  100                 105                 110 ggc gag gct gcc gag ccc ggc tcg gcc acg gcc gcg gag gga gag gcc      747
Gly Glu Ala Ala Glu Pro Gly Ser Ala Thr Ala Ala Glu Gly Glu Ala
             115                 120                 125 gcg tcg gcc gcc tcc tcg act tct tcg ccc aag gcc gag gac ggg gcc      795
Ala Ser Ala Ala Ser Ser Thr Ser Ser Pro Lys Ala Glu Asp Gly Ala
         130                 135                 140 acg ccc tcg ccc agc aac gag acc ccg aaa aaa aaa aag aag cgc ttt      843
Thr Pro Ser Pro Ser Asn Glu Thr Pro Lys Lys Lys Lys Lys Arg Phe
 145                 150                 155 tcc ttc aag aag tct ttc aag ctg agc ggc ttc tcc ttc aag aag aac      891
Ser Phe Lys Lys Ser Phe Lys Leu Ser Gly Phe Ser Phe Lys Lys Asn
 160                 165                 170 aag aag gag gct gga gaa ggc ggt gag gct gag gcg ccc gct gcc gaa      939
Lys Lys Glu Ala Gly Glu Gly Gly Glu Ala Glu Ala Pro Ala Ala Glu
 175                 180                 185                 190 ggc ggc aag gac gag gcc gcc ggg ggc gca gct gcg gcc gcc gcc gag      987
Gly Gly Lys Asp Glu Ala Ala Gly Gly Ala Ala Ala Ala Ala Ala Glu
             195                 200                 205 gcg ggc gcg gcc tcc ggg gag cag gca gcg gcg ccg ggc gag gag gcg      1035
Ala Gly Ala Ala Ser Gly Glu Gln Ala Ala Ala Pro Gly Glu Glu Ala
         210                 215                 220 gca gcg ggc gag gag ggg gcg gcg ggt ggc gac ccg cag gag gcc aag      1083
Ala Ala Gly Glu Glu Gly Ala Ala Gly Gly Asp Pro Gln Glu Ala Lys
 225                 230                 235 ccc cag gag gcc gct gtc gcg cca gag aag ccg ccc gcc agc gac gag      1131
Pro Gln Glu Ala Ala Val Ala Pro Glu Lys Pro Pro Ala Ser Asp Glu
 240                 245                 250
```

-continued

```
acc aag gcc gcc gag gag ccc agc aag gtg gag gag aaa aag gcc gag     1179
Thr Lys Ala Ala Glu Glu Pro Ser Lys Val Glu Glu Lys Lys Ala Glu
255                 260                 265                 270 gag gcc ggg gcc agc gcc gcc gcc tgc gag gcc ccc tcc gcc gcc ggg     1227
Glu Ala Gly Ala Ser Ala Ala Ala Cys Glu Ala Pro Ser Ala Ala Gly
            275                 280                 285 ccc ggc gcg ccc ccg gag cag gag gca gcc ccc gcg gag gag ccc gcg     1275
Pro Gly Ala Pro Pro Glu Gln Glu Ala Ala Pro Ala Glu Glu Pro Ala
290                 295                 300 gcc gcc gca gcc tcg tca gcc tgc gca gcc ccc tca cag gag gcc cag     1323
Ala Ala Ala Ala Ser Ser Ala Cys Ala Ala Pro Ser Gln Glu Ala Gln
        305                 310                 315 ccc gag tgc agt cca gaa gcc ccc cca gcg gag gcg gca gag taa         1368
Pro Glu Cys Ser Pro Glu Ala Pro Pro Ala Glu Ala Ala Glu
320                 325                 330 aagagcaagc ttttgtgaga aatcgaaga acttttctcc cccgtttgtt tgttggagtg    1428
gtgccaggta ctgttttgga gaacttgtct acaaccaggg attgatttta agatgtctt    1488
tttttatttt actttttttt aagcaccaaa ttttgttgtt ttttttttc tcccctcccc    1548
acagatccca tctcaaatca ttctgttaac caccattcca acaggtcgag gagagcttaa   1608
acaccttctt cctctgcctt gtttctcttt tattttttat ttttcgcat cagtattaat    1668
gtttttgcat actttgcatc tttattcaaa agtgtaaact ttctttgtca atctatggac   1728
atgcccatat atgaaggaga tgggtgggtc aaaaagggat atcaaatgaa gtgatagggg   1788
tcacaatggg gaaattgaag tggtgcataa cattgccaaa atagtgtgcc actagaaatg   1848
gtgtaaaggc tgtcttttt ttttttttta agaaaagtt attaccatgt attttgtgag    1908
gcaggtttac aacactacaa gtcttgagtt aagaaggaaa gaggaaaaaa gaaaaaacac   1968
caatacccag atttaaaaaa aaaaaaacga tcatagtctt aggagttcat ttaaaccata   2028
ggaacttttc acttatctca tgttagctgt accagtcagt gattaagtag aactacaagt   2088
tgtataggct ttattgttta ttgctggttt atgaccttaa taaagtgtaa ttatgtatta   2148
ccagcagggt gttttaact gtgactattg tataaaaaca aatcttgata tccagaagca    2208
catgaagttt gcaactttcc accctgccca tttttgtaaa actgcagtca tcttggacct   2268
tttaaaacac aaatttaaa ctcaaccaag ctgtgataag tggaatggtt actgttata    2328
ctgtggtatg ttttgatta cagcagataa tgctttcttt tccagtcgtc tttgagaata   2388
aaggaaaaaa aatcttcaga tgcaatggtt ttgtgtagca tcttgtctat catgttttgt   2448
aaatactgga gaagctttga ccaatttgac ttagagatgg aatgtaactt tgcttacaaa   2508
aattgctatt aaactcctgc ttaaggtgtt ctaattttct gtgagcacac taaaagcgaa   2568
aaataaatgt gaataaaatg t                                            2589
```

<210> SEQ ID NO 6
<211> LENGTH: 332
<212> TYPE: PRT
<213> ORGANISM: Homo Sapiens

<400> SEQUENCE: 6

```
Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
        35                  40                  45
```

-continued

```
Ala Ala Glu Ser Gly Ala Lys Glu Glu Leu Gln Ala Asn Gly Ser Ala
        50              55              60

Pro Ala Ala Asp Lys Glu Pro Ala Ala Gly Ser Gly Ala Ala
65              70              75              80

Ser Pro Ser Ser Ala Glu Lys Gly Glu Pro Ala Ala Ala Ala Pro
                85              90              95

Glu Ala Gly Ala Ser Pro Val Glu Lys Glu Ala Pro Ala Glu Gly Glu
            100             105             110

Ala Ala Glu Pro Gly Ser Ala Thr Ala Ala Glu Gly Glu Ala Ala Ser
        115             120             125

Ala Ala Ser Ser Thr Ser Pro Lys Ala Glu Asp Gly Ala Thr Pro
        130             135             140

Ser Pro Ser Asn Glu Thr Pro Lys Lys Lys Lys Arg Phe Ser Phe
145             150             155             160

Lys Lys Ser Phe Lys Leu Ser Gly Phe Ser Phe Lys Lys Asn Lys Lys
            165             170             175

Glu Ala Gly Glu Gly Gly Glu Ala Glu Ala Pro Ala Ala Glu Gly Gly
            180             185             190

Lys Asp Glu Ala Ala Gly Gly Ala Ala Ala Ala Ala Glu Ala Gly
        195             200             205

Ala Ala Ser Gly Glu Gln Ala Ala Pro Gly Glu Glu Ala Ala Ala
        210             215             220

Gly Glu Glu Gly Ala Ala Gly Gly Asp Pro Gln Glu Ala Lys Pro Gln
225             230             235             240

Glu Ala Ala Val Ala Pro Glu Lys Pro Pro Ala Ser Asp Glu Thr Lys
            245             250             255

Ala Ala Glu Glu Pro Ser Lys Val Glu Glu Lys Lys Ala Glu Glu Ala
            260             265             270

Gly Ala Ser Ala Ala Ala Cys Glu Ala Pro Ser Ala Ala Gly Pro Gly
        275             280             285

Ala Pro Pro Glu Gln Glu Ala Ala Pro Ala Glu Glu Pro Ala Ala Ala
        290             295             300

Ala Ala Ser Ser Ala Cys Ala Ala Pro Ser Gln Glu Ala Gln Pro Glu
305             310             315             320

Cys Ser Pro Glu Ala Pro Pro Ala Glu Ala Ala Glu
            325             330
```